US006936604B2

(12) United States Patent
Dyatkin et al.

(10) Patent No.: US 6,936,604 B2
(45) Date of Patent: Aug. 30, 2005

(54) BRIDGED BICYCLIC AMINO ACID-DERIVED [1,4]BENZODIAZEPINE VASOPRESSIN RECEPTOR ANTAGONISTS

(75) Inventors: Alexey B. Dyatkin, Ambler, PA (US); William J. Hoekstra, Chapel Hill, NC (US); Bruce E. Maryanoff, Forest Grove, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/269,656

(22) Filed: Oct. 11, 2002

(65) Prior Publication Data
US 2003/0119822 A1 Jun. 26, 2003

Related U.S. Application Data
(60) Provisional application No. 60/341,049, filed on Oct. 29, 2001.

(51) Int. Cl.$^7$ .................. C07D 487/08; C07D 221/00; C07D 243/00; C07D 209/00; A61K 31/55
(52) U.S. Cl. .................. 514/219; 514/220; 540/555; 540/556; 540/58; 540/559
(58) Field of Search ................. 540/555, 556, 540/558, 559; 514/219, 220

(56) References Cited

U.S. PATENT DOCUMENTS

| | | | |
|---|---|---|---|
| 3,860,600 A | 1/1975 | Carabateas | 260/293.55 |
| 5,258,510 A | 11/1993 | Ogawa et al. | |
| 5,521,173 A | 5/1996 | Venkatesan et al. | 514/220 |
| 5,559,230 A | 9/1996 | Ogawa et al. | |
| 5,700,796 A | 12/1997 | Albright et al. | 514/220 |
| 5,985,869 A | 11/1999 | Ogawa et al. | |
| 6,713,475 B2 | 3/2004 | Hoekstra et al. | |

FOREIGN PATENT DOCUMENTS

| EP | 0 987 266 A1 | 3/2000 |
|---|---|---|
| WO | WO 00 43398 A | 7/2000 |

OTHER PUBLICATIONS

Trybulski; Annual Reports in Medicinal Chemistry–36, Chapter 16 "Vasopressin Receptor Modulators: From Non–peptide Antagonists to Agonists" (2001).*
PCT International Search Report PCT/US02/32789 dated Jan. 9, 2003.
Ohtake, Y. et al; "Novel Vasopressin V2 Receptor–selective Antagonists, Pyrrolo[2,1–a]quinoxaline and Pyrrolo[2,1–c][1,4]benzodiazepine Derivatives"; Bioorganic & Medicinal Chemistry, 1999; pp. 1247–1254; vol. 7, No. 6; Elsevier Science Ltd.; XP002225041.
Dyatkin, Alexey B., et al., "Bridged Bicyclic Vasopressin Receptor Antagonists with $V_2$ Selective or Dual $V_{1a}/V_2$ Activity", Bioorganic & Medicinal Chemistry Letters, vol. 12, Issue 21, Nov. 4, 2002, pp 3081–3084.
Van Zwieten, P.A., Progr. Pharmacol. Clin. Pharmacol. 1990, 7, 49–66.
Ogawa, H., J. Med. Chem. 1996, 39, 3547–3555.
Fujisawa, G., Kidney Int. 1993, 44(1), 19–23.
Ref. International J. Pharm., 1986, 33, 201–217.
J. Pharm. Sci., 1997 (Jan), 86, 1, 1–12.
Hamley et al., in Synlett, 1991,29–30.
Bailey, P.D., et al., Tetrahedron: Asymmetry, 1991, 2(12), 1263–1282.
Bailey, P.D., et al., Tetrahedron Letters, 1989, 30(48), 6781–6784.
Campbell, J.A., et al., J. Org. Chem. 1996, 61, 6313–6325.

* cited by examiner

*Primary Examiner*—Bruck Kifle
(74) *Attorney, Agent, or Firm*—Gabriel Lopez; Hal B. Woodrow

(57) ABSTRACT

The invention is directed to bridged bicyclic amino acid-derived [1,4]benzodiazepine compounds, intermediates and pharmaceutical compositions thereof useful as vasopressin receptor antagonists and methods for treating vasopressin mediated disorders.

48 Claims, No Drawings

BRIDGED BICYCLIC AMINO ACID-DERIVED [1,4]BENZODIAZEPINE VASOPRESSIN RECEPTOR ANTAGONISTS

This application claims priority of non-provisional application Ser. No. 60/341,049, filed Oct. 29, 2001, which is hereby incorporated by reference.

FIELD OF THE INVENTION

This invention is directed to certain novel compounds, their synthesis and their use as vasopressin receptor antagonists. More particularly, this invention is directed to bridged bicyclic amino acid-derived [1,4]benzodiazepine compounds useful as vasopressin receptor antagonists and methods for treating vasopressin mediated disorders.

BACKGROUND OF THE INVENTION

Vasopressin is a nonapeptide hormone that is secreted primarily from the posterior pituitary gland. The hormone effects its actions through the vascular $V_{1a}$ and $V_{1b}$ receptor subtypes and the renal $V_2$ receptor subtype. The functions of vasopressin include contraction of uterine, bladder and smooth muscle, stimulation of glycogen breakdown in the liver, release of corticotropin from the anterior pituitary, induction of platelet aggregation and central nervous system modulation of behaviors and stress responses. The $V_{1a}$ receptor mediates the contraction of smooth muscle and the hepatic glycogenolytic and central nervous system effects of vasopressin. The $V_2$ receptor, presumably found only in the kidney, effects the antidiuretic actions of vasopressin via stimulation of adenylate cyclase.

Elevated plasma vasopressin levels appear to play a role in the pathogenesis of congestive heart failure (P. A. Van Zwieten, *Progr. Pharmacol. Clin. Pharmacol.* 1990, 7, 49). As progress toward the treatment of congestive heart failure, nonpeptide vasopressin $V_2$ receptor antagonists have induced low osmolality aquaresis and decreased peripheral resistance in conscious dogs with congestive heart failure (H. Ogawa, *J. Med. Chem.* 1996, 39, 3547). In certain pathological states, plasma vasopressin levels may be inappropriately elevated for a given osmolality, thereby resulting in renal water retention and hyponatremia. Hyponatremia, associated with edematous conditions (cirrhosis, congestive heart failure, renal failure), can be accompanied by the syndrome of inappropriate secretion of antidiuretic hormone (SIADH). Treatment of SIADH-compromised rats with a vasopressin $V_2$ antagonist has corrected their existing hyponatremia (G. Fujisawa, *Kidney Int.* 1993, 44(1), 19). Due in part to the contractile actions of vasopressin at its $V_{1a}$ receptor in the vasculature, vasopressin $V_{1a}$ antagonists have reduced blood pressure as a potential treatment for hypertension as well. Thus, vasopressin receptor antagonists could be useful as therapeutics in the conditions of hypertension, congestive heart failure/cardiac insufficiency, coronary vasospasm, cardiac ischemia, liver cirrhosis, renal vasospasm, renal failure, cerebral edema and ischemia, stroke, thrombosis, and water retention.

U.S. Pat. No. 3,860,600 relates to heterocyclo[1,4] benzodiazepine derivatives of the formula:

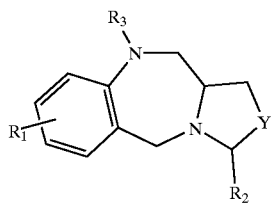

wherein $R_1$ is hydrogen or methylenedioxy attached to adjacent carbon atoms or from one to three members of the group consisting of lower-alkyl, lower-alkoxy, fluorine, chlorine, di-lower-alkylamino, N-lower-alkyl-N-lower-alkanoylamino, hydroxy and benzyloxy; $R_2$ is a member of the group consisting of hydrogen, hydroxymethyl or lower-alkanoyloxymethyl; $R_3$ is lower-alkyl, lower-alkanoyl, α-lower-alkanoyloxy-lower-alkanoyl, benzoyl, benzyl or benzoyl or benzyl substituted by methylenedioxy attached to adjacent carbon atoms or from one to three members of the group consisting of lower-alkyl, lower-alkoxy, fluorine, chlorine, lower-alkylmercapto, lower-alkylsulfinyl, lower-alkylsulfonyl or hydroxy; and Y is one of the groups: —CH$_2$—, —CH(OR$_4$)—, —CH$_2$CH$_2$—, —CH(CH$_2$OR$_4$)CH$_2$—, —S—, —SO—, —SO$_2$—, —CH=CH—, or

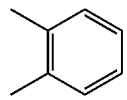

(i.e., o-phenylene), where $R_4$ is hydrogen or lower-alkanoyl.

European Patent Application EP 0987266 A1 relates to biphenyl derivatives of the formula and pharmaceutically acceptable salts thereof:

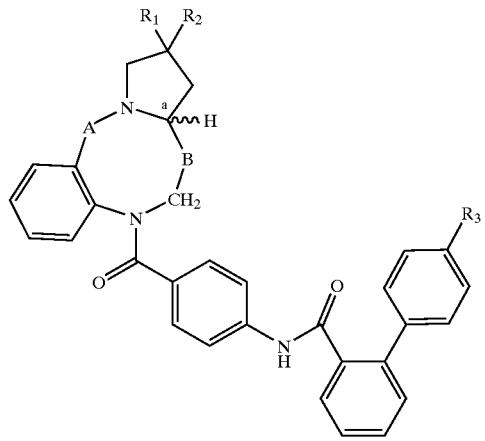

wherein A represents a single bond, —CH$_2$—, —CO—, —CS— or —SO$_2$—; B represents a single bond or a group —CH$_2$—; $R_1$ represents a hydrogen atom, —OH, —NR$_{11}$R$_{12}$ (wherein $R_{11}$ and $R_{12}$ each independently represents a hydrogen atom or an alkyl group having 1 to 4 carbon atoms), —OCOCH$_3$ or a halogen atom; $R_2$ represents a hydrogen atom or $R_1$ and $R_2$ represent =O, in combination; $R_3$ represents a hydrogen atom or an alkyl group having 1 to 4 carbon atoms; provided that the absolute configuration at the position a may be either S or R.

Accordingly, it is an object of the present invention to provide bridged bicyclic amino acid-derived [1,4] benzodiazepine compounds that are vasopressin receptor antagonists. It is an object of the invention to provide a method for using a compound of the present invention for treating vasopressin mediated disorders.

SUMMARY OF THE INVENTION

The present invention is directed to bridged bicyclic amino acid-derived [1,4]benzodiazepine compounds of Formula (I):

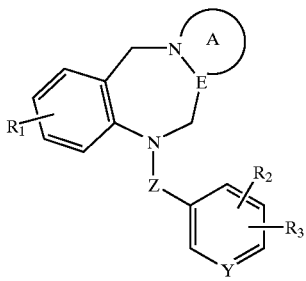

Formula (I)

wherein

A is a bridged bicycloalkyl ring system of 4 to 7 carbon atoms formed with a nitrogen atom of attachment and E;

E is selected from the group consisting of a). a —C— atom of attachment bonded to the nitrogen atom of attachment and two carbon atoms of the bridged bicycloalkyl ring system and b). a —CH— atom of attachment bonded to the nitrogen atom of attachment and one carbon atom of the bridged bicycloalkyl ring system;

$R_1$ is one to four substituents independently selected from the group consisting of hydrogen, $C_{1-8}$alkyl (optionally substituted on a terminal carbon atom with a substituent selected from the group consisting of aryl, heteroaryl, hydroxy and (halo)$_{1-3}$), $C_{1-8}$alkoxy (optionally substituted on a terminal carbon atom with a substituent selected from the group consisting of hydroxy and (halo)$_{1-3}$), $C_{2-8}$alkenyl, $C_{2-8}$alkynyl, aryl, heteroaryl, halogen and hydroxy;

$R_2$ is selected from the group consisting of —NR$_4$COAr, —NR$_4$CO-heteroaryl, —NR$_4$Ar, —CH=CH—Ar, —CF=CH—Ar, —CH=CF—Ar, —CCl=CH—Ar, —CH=CCl—Ar, —CH=CH-heteroaryl, —CF=CH-heteroaryl, —CH=CF-heteroaryl, —CCl=CH-heteroaryl, —CH=CCl-heteroaryl, —OCH$_2$—Ar, —OCH$_2$-heteroaryl, —SCH$_2$—Ar and —NR$_4$CH$_2$Ar;

Ar is selected from the group consisting of aryl and heteroaryl optionally substituted with one to five substituents independently selected from the group consisting of $C_{1-8}$alkyl (optionally substituted on a terminal carbon atom with a substituent selected from the group consisting of aryl, heteroaryl, amino (optionally substituted with one to two substituents selected from $C_{1-8}$alkyl), hydroxy and (halo)$_{1-3}$), $C_{1-8}$alkoxy (optionally substituted on a terminal carbon atom with a substituent selected from the group consisting of aryl, hydroxy and (halo)$_{1-3}$), aryl, heteroaryl, carboxyl, amino (optionally substituted with one to two substituents selected from $C_{1-8}$ alkyl), $C_{1-8}$ alkylsulfonyl, $C_{1-8}$ alkylsulfinyl, thio (substituted with a substituent selected from the group consisting of $C_{1-8}$alkyl and (halo)$_{1-3}$($C_{1-8}$)alkyl), cyano, halogen, hydroxy and nitro; wherein aryl, heteroaryl and the aryl and heteroaryl portions of any of the foregoing substituents are optionally substituted with one to four substituents independently selected from the group consisting of $C_{1-8}$alkyl (optionally substituted on a terminal carbon atom with a substituent selected from the group consisting of amino (optionally substituted with one to two substituents selected from $C_{1-8}$alkyl), hydroxy and (halo)$_{1-3}$), $C_{1-8}$alkoxy (optionally substituted on a terminal carbon atom with a substituent selected from the group consisting of hydroxy and (halo)$_{1-3}$), carboxyl, amino (optionally substituted with one to two substituents selected from $C_{1-8}$ alkyl), $C_{1-8}$ alkylsulfonyl, $C_{1-8}$ alkylsulfinyl, $C_{1-8}$ alkylthio, cyano, halogen, hydroxy and nitro;

$R_3$ is one to three substituents independently selected from the group consisting of hydrogen, $C_{1-8}$alkyl (optionally substituted on a terminal carbon atom with a substituent selected from the group consisting of amino (optionally substituted with one to two substituents selected from $C_{1-8}$alkyl), hydroxy and (halo)$_{1-3}$), $C_{1-8}$alkoxy (optionally substituted on a terminal carbon atom with a substituent selected from the group consisting of hydroxy and (halo)$_{1-3}$), amino (optionally substituted with one to two substituents selected from $C_{1-8}$ alkyl), halogen and hydroxy;

$R_4$ is selected from the group consisting of hydrogen and $C_{1-8}$ alkyl;

Y is selected from the group consisting of CH and N; and,

Z is selected from the group consisting of CH$_2$, CH, —C(O)— and —SO$_2$—;

and pharmaceutically acceptable salts, racemic mixtures, diastereomers and enantiomers thereof.

Embodiments of the present invention include a method for treating vasopressin mediated disorders comprising administering to a subject in need thereof a therapeutically effective amount of a compound of Formula (I) or a pharmaceutical composition comprising a mixture of a compound of Formula (I) and a pharmaceutically acceptable carrier.

Embodiments of the present invention include the use of a compound of Formula (I) for the preparation of a medicament for treating vasopressin mediated disorders in a subject in need thereof.

DETAILED DESCRIPTION OF THE INVENTION

Preferred embodiments of the present invention include a compound of Formula (I) wherein $R_1$ is one to four substituents independently selected from the group consisting of hydrogen, $C_{1-4}$alkyl (optionally substituted on a terminal carbon atom with a substituent selected from the group consisting of hydroxy and (halo)$_{1-3}$), $C_{1-4}$alkoxy (optionally substituted on a terminal carbon atom with a substituent selected (halo)$_{1-3}$), halogen and hydroxy.

More preferably, $R_1$ is one to two substituents independently selected from the group consisting of hydrogen, methyl, methoxy, chlorine, fluorine and hydroxy.

Most preferably, $R_1$ is selected from the group consisting of hydrogen, chlorine and fluorine.

Preferred embodiments of the present invention include a compound of Formula (I) wherein $R_2$ is selected from the group consisting of —NR$_4$COAr, —NR$_4$CO-heteroaryl, —NR$_4$Ar, —CH=CH—Ar, —CF=CH—Ar, —CH=CF—Ar, —CCl=CH—Ar, —CH=CCl—Ar, —CH=CH-heteroaryl, —CF=CH-heteroaryl, —CH=CF-heteroaryl, —CCl=CH-heteroaryl, —CH=CCl-heteroaryl and —NR$_4$CH$_2$Ar.

More preferably, $R_2$ is selected from the group consisting of —NR$_4$COAr.

Most preferably, $R_2$ is selected from the group consisting of —NHCOAr.

Preferred embodiments of the present invention include a compound of Formula (I) wherein Ar is selected from the group consisting of phenyl and naphthyl optionally substituted with one to four substituents independently selected from the group consisting of $C_{1-8}$alkyl (optionally substituted on a terminal carbon atom with a substituent selected from the group consisting of aryl, heteroaryl, amino (optionally substituted with one to two substituents selected from $C_{1-8}$alkyl), hydroxy and (halo)$_{1-3}$), $C_{1-8}$alkoxy (optionally substituted on a terminal carbon atom with a substituent selected from the group consisting of aryl, hydroxy and (halo)$_{1-3}$), aryl, heteroaryl, amino (optionally substituted with one to two substituents selected from $C_{1-8}$ alkyl), halogen and hydroxy; wherein aryl, heteroaryl and the aryl and heteroaryl portions of any of the foregoing substituents are optionally substituted with one to four substituents independently selected from the group consisting of $C_{1-8}$alkyl (optionally substituted on a terminal carbon atom with a substituent selected from the group consisting of amino (optionally substituted with one to two substituents selected from $C_{1-8}$alkyl), hydroxy and (halo)$_{1-3}$), $C_{1-8}$alkoxy (optionally substituted on a terminal carbon atom with a substituent selected from the group consisting of hydroxy and (halo)$_{1-3}$), amino (optionally substituted with one to two substituents selected from $C_{1-8}$ alkyl), $C_{1-8}$ alkylsulfonyl, $C_{1-8}$ alkylsulfinyl, $C_{1-8}$ alkylthio, cyano, halogen and hydroxy.

More preferably, Ar is phenyl optionally substituted with one to four substituents independently selected from the group consisting of $C_{1-4}$alkyl (optionally substituted on a terminal carbon atom with a substituent selected from the group consisting of amino (optionally substituted with one to two substituents selected from $C_{1-4}$alkyl), hydroxy and (halo)$_{1-3}$), $C_{1-4}$alkoxy (optionally substituted on a terminal carbon atom with a substituent selected from the group consisting of hydroxy and (halo)$_{1-3}$), aryl, heteroaryl, amino (optionally substituted with one to two substituents selected from $C_{1-4}$ alkyl), halogen and hydroxy; wherein the aryl and heteroaryl substituents are optionally substituted with one to four substituents independently selected from the group consisting of $C_{1-4}$alkyl (optionally substituted on a terminal carbon atom with a substituent selected from the group consisting of hydroxy and (halo)$_{1-3}$), $C_{1-4}$alkoxy (optionally substituted on a terminal carbon atom with a substituent selected from the group consisting of hydroxy and (halo)$_{1-3}$), amino (optionally substituted with one to two substituents selected from $C_{1-4}$ alkyl), halogen and hydroxy.

Most preferably, Ar is phenyl optionally substituted with one to two substituents independently selected from the group consisting of $C_{1-4}$alkyl, phenyl, halogen and trifluoro($C_{1-4}$)alkyl; wherein phenyl is optionally substituted with a substituent selected from the group consisting of $C_{1-4}$alkyl and halogen.

Preferred embodiments of the present invention include a compound of Formula (I) wherein $R_3$ is one to two substituents independently selected from the group consisting of hydrogen, $C_{1-4}$alkyl (optionally substituted on a terminal carbon atom with a substituent selected from the group consisting of amino (optionally substituted with one to two substituents selected from $C_{1-4}$alkyl), hydroxy and (halo)$_{1-3}$), $C_{1-4}$alkoxy (optionally substituted on a terminal carbon atom with a substituent selected from the group consisting of hydroxy and (halo)$_{1-3}$), amino (optionally substituted with one to two substituents selected from $C_{1-4}$ alkyl), halogen and hydroxy.

More preferably, $R_3$ is one to two substituents independently selected from the group consisting of hydrogen, $C_{1-4}$ alkyl, trifluoro($C_{1-4}$)alkyl, $C_{1-4}$ alkoxy, trifluoro($C_{1-4}$) alkoxy, halogen and hydroxy.

Most preferably, $R_3$ is one to two substituents independently selected from the group consisting of hydrogen, methoxy, chlorine, fluorine and hydroxy.

Preferred embodiments of the present invention include a compound of Formula (I) wherein $R_4$ is selected from the group consisting of hydrogen and $C_{1-4}$ alkyl.

More preferably, $R_4$ is selected from hydrogen.

Preferred embodiments of the present invention include a compound of Formula (I) wherein Y is CH.

Preferred embodiments of the present invention include a compound of Formula (I) wherein Z is —C(O)—.

A preferred embodiment of the present invention is directed to a compound of Formula (I) wherein the compound is selected from the group consisting of a compound of Formula (II), Formula (III) and Formula (IV):

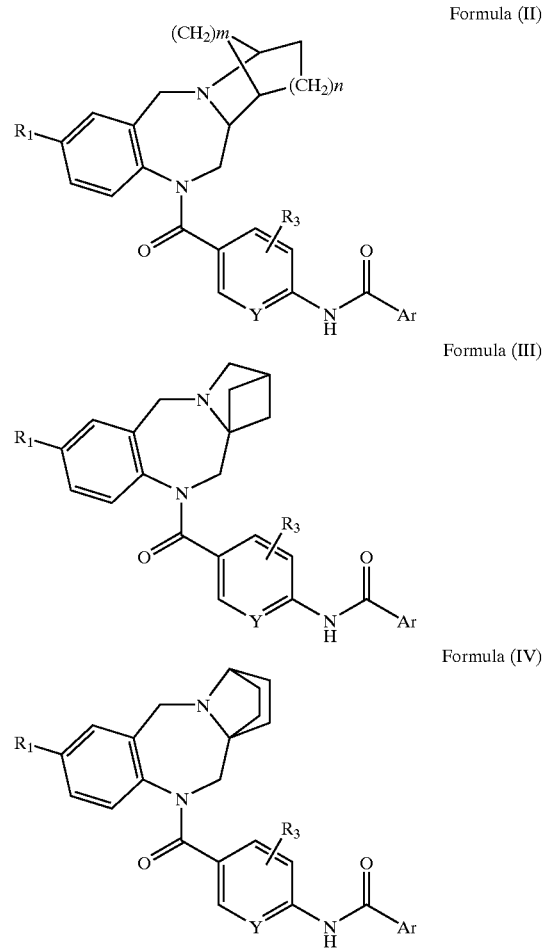

Formula (II)

Formula (III)

Formula (IV)

wherein $R_1$ is one to four substituents independently selected from the group consisting of hydrogen, $C_{1-8}$alkyl (optionally substituted on a terminal carbon atom with a substituent selected from the group consisting of aryl, heteroaryl, hydroxy and (halo)$_{1-3}$), $C_{1-8}$alkoxy (optionally substituted on a terminal carbon atom with a substituent selected from the group consisting of hydroxy and (halo)$_{1-3}$), $C_{2-8}$alkenyl, $C_{2-8}$alkynyl, aryl, heteroaryl, halogen and hydroxy;

Ar is selected from the group consisting of aryl and heteroaryl optionally substituted with one to five substituents independently selected from the group consisting of $C_{1-8}$alkyl (optionally substituted on a terminal carbon atom with a substituent selected from the group consisting of aryl, heteroaryl, amino (optionally substituted with one to two substituents selected from $C_{1-8}$alkyl), hydroxy and (halo)$_{1-3}$), C$_{1-8}$alkoxy (optionally substituted on a terminal carbon atom with a substituent selected from the group consisting of aryl, hydroxy and (halo)$_{1-3}$), aryl, heteroaryl, carboxyl, amino (optionally substituted with one to two substituents selected from C$_{1-8}$ alkyl), C$_{1-8}$ alkylsulfonyl, C$_{1-8}$ alkylsulfinyl, thio (substituted with a substituent selected from the group consisting of C$_{1-8}$alkyl and (halo)$_{1-3}$(C$_{1-8}$)alkyl), cyano, halogen, hydroxy and nitro; wherein aryl, heteroaryl and the aryl and heteroaryl portions of any of the foregoing substituents are optionally substituted with one to four substituents independently selected from the group consisting of C$_{1-8}$alkyl (optionally substituted on a terminal carbon atom with a substituent selected from the group consisting of amino (optionally substituted with one to two substituents selected from C$_{1-8}$alkyl), hydroxy and (halo)$_{1-3}$), C$_{1-8}$alkoxy (optionally substituted on a terminal carbon atom with a substituent selected from the group consisting of hydroxy and (halo)$_{1-3}$), carboxyl, amino (optionally substituted with one to two substituents selected from C$_{1-8}$ alkyl), C$_{1-8}$ alkylsulfonyl, C$_{1-8}$ alkylsulfinyl, C$_{1-8}$ alkylthio, cyano, halogen, hydroxy and nitro;

R$_3$ is one to three substituents independently selected from the group consisting of hydrogen, C$_{1-8}$alkyl (optionally substituted on a terminal carbon atom with a substituent selected from the group consisting of amino (optionally substituted with one to two substituents selected from C$_{1-8}$alkyl), hydroxy and (halo)$_{1-3}$), C$_{1-8}$alkoxy (optionally substituted on a terminal carbon atom with a substituent selected from the group consisting of hydroxy and (halo)$_{1-3}$), amino (optionally substituted with one to two substituents selected from C$_{1-8}$ alkyl), halogen and hydroxy; and, Y is selected from the group consisting of CH and N; and, m is an integer selected from 1 or 2; and, n is an integer selected from 0, 1 or 2;

and pharmaceutically acceptable salts, racemic mixtures, diastereomers and enantiomers thereof.

Preferred embodiments of the present invention include a compound selected from the group consisting of a compound of Formula (II), Formula (III) and Formula (IV) wherein R$_1$ is one to four substituents independently selected from the group consisting of hydrogen, C$_{1-4}$alkyl (optionally substituted on a terminal carbon atom with a substituent selected from the group consisting of hydroxy and (halo)$_{1-3}$), C$_{1-4}$alkoxy (optionally substituted on a terminal carbon atom with a substituent selected (halo)$_{1-3}$), halogen and hydroxy.

More preferably, R$_1$ is one to two substituents independently selected from the group consisting of hydrogen, methyl, methoxy, chlorine, fluorine and hydroxy.

Most preferably, R$_1$ is selected from the group consisting of hydrogen, chlorine and fluorine.

Preferred embodiments of the present invention include a compound selected from the group consisting of a compound of Formula (II), Formula (III) and Formula (IV) wherein Ar is selected from the group consisting of phenyl and naphthyl optionally substituted with one to four substituents independently selected from the group consisting of C$_{1-8}$alkyl (optionally substituted on a terminal carbon atom with a substituent selected from the group consisting of aryl, heteroaryl, amino (optionally substituted with one to two substituents selected from C$_{1-8}$alkyl), hydroxy and (halo)$_{1-3}$), C$_{1-8}$alkoxy (optionally substituted on a terminal carbon atom with a substituent selected from the group consisting of aryl, hydroxy and (halo)$_{1-3}$), aryl, heteroaryl, amino (optionally substituted with one to two substituents selected from C$_{1-8}$ alkyl), halogen and hydroxy; wherein aryl, heteroaryl and the aryl and heteroaryl portions of any of the foregoing substituents are optionally substituted with one to four substituents independently selected from the group consisting of C$_{1-8}$alkyl (optionally substituted on a terminal carbon atom with a substituent selected from the group consisting of amino (optionally substituted with one to two substituents selected from C$_{1-8}$alkyl), hydroxy and (halo)$_{1-3}$), C$_{1-8}$alkoxy (optionally substituted on a terminal carbon atom with a substituent selected from the group consisting of hydroxy and (halo)$_{1-3}$), amino (optionally substituted with one to two substituents selected from C$_{1-8}$ alkyl), C$_{1-8}$ alkylsulfonyl, C$_{1-8}$ alkylsulfinyl, C$_{1-8}$ alkylthio, cyano, halogen and hydroxy.

More preferably, Ar is phenyl optionally substituted with one to four substituents independently selected from the group consisting of C$_{1-4}$alkyl (optionally substituted on a terminal carbon atom with a substituent selected from the group consisting of amino (optionally substituted with one to two substituents selected from C$_{1-4}$alkyl), hydroxy and (halo)$_{1-3}$), C$_{1-4}$alkoxy (optionally substituted on a terminal carbon atom with a substituent selected from the group consisting of hydroxy and (halo)$_{1-3}$), aryl, heteroaryl, amino (optionally substituted with one to two substituents selected from C$_{1-4}$ alkyl), halogen and hydroxy; wherein the aryl and heteroaryl substituents are optionally substituted with one to four substituents independently selected from the group consisting of C$_{1-4}$alkyl (optionally substituted on a terminal carbon atom with a substituent selected from the group consisting of hydroxy and (halo)$_{1-3}$), C$_{1-4}$alkoxy (optionally substituted on a terminal carbon atom with a substituent selected from the group consisting of hydroxy and (halo)$_{1-3}$), amino (optionally substituted with one to two substituents selected from C$_{1-4}$ alkyl), halogen and hydroxy.

Most preferably, Ar is phenyl optionally substituted with one to two substituents independently selected from the group consisting of C$_{1-4}$alkyl, phenyl, halogen and trifluoro(C$_{1-4}$)alkyl; wherein phenyl is optionally substituted with a substituent selected from the group consisting of C$_{1-4}$alkyl and halogen.

Preferred embodiments of the present invention include a compound selected from the group consisting of a compound of Formula (II), Formula (III) and Formula (IV) wherein R$_3$ is one to two substituents independently selected from the group consisting of hydrogen, C$_{1-4}$alkyl (optionally substituted on a terminal carbon atom with a substituent selected from the group consisting of amino (optionally substituted with one to two substituents selected from C$_{1-4}$alkyl), hydroxy and (halo)$_{1-3}$), C$_{1-4}$alkoxy (optionally substituted on a terminal carbon atom with a substituent selected from the group consisting of hydroxy and (halo)$_{1-3}$), amino (optionally substituted with one to two substituents selected from C$_{1-4}$ alkyl), halogen and hydroxy.

More preferably, R$_3$ is one to two substituents independently selected from the group consisting of hydrogen, C$_{1-4}$ alkyl, trifluoro(C$_{1-4}$)alkyl, C$_{1-4}$ alkoxy, trifluoro(C$_{1-4}$) alkoxy, halogen and hydroxy.

Most preferably, R$_3$ is one to two substituents independently selected from the group consisting of hydrogen, methoxy, chlorine, fluorine and hydroxy.

Preferred embodiments of the present invention include a compound selected from the group consisting of a compound of Formula (II), Formula (III) and Formula (IV) wherein Y is CH.

Preferred embodiments of the present invention include a compound of Formula (II) wherein n is an integer selected from 1 or 2.

More preferably, n is 1.

Exemplified compounds of the present invention include a compound of Formula (IIa):

TABLE 1

Formula (IIa)

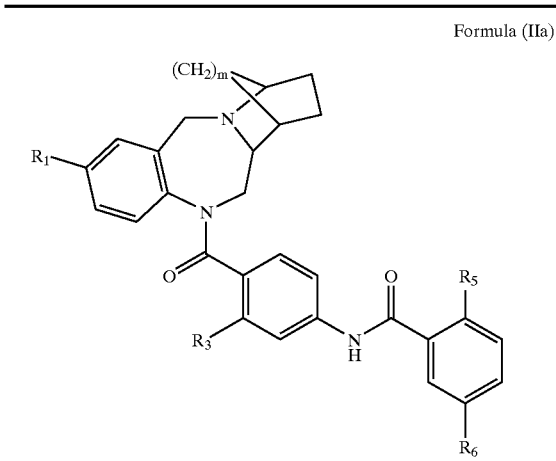

wherein m, $R_1$, $R_3$, $R_5$ and $R_6$ are dependently selected from:

| Cpd | m | $R_1$ | $R_3$ | $R_5$ | $R_6$ | *Absolute Configuration |
|---|---|---|---|---|---|---|
| 1 | 2 | H | H | Ph | H | Racemate |
| 2 | 2 | H | Cl | Ph | H | Racemate |
| 3 | 1 | H | Cl | Ph | H | Racemate |
| 4 | 1 | H | Cl | Ph | H | S |
| 5 | 1 | H | Cl | Ph | H | R |
| 6 | 1 | Cl | H | 4-Me-Ph | H | S |
| 7 | 1 | H | Cl | 4-Me-Ph | H | S |
| 8 | 1 | Cl | Cl | 4-Me-Ph | H | S |
| 9 | 1 | Cl | H | 4-F-Ph | H | S |
| 10 | 1 | Cl | H | F | H | S |
| 11 | 1 | Cl | H | Cl | H | S |
| 12 | 1 | Cl | H | $CF_3$ | H | S |
| 13 | 2 | H | Cl | Ph | H | S |
| 14 | 2 | H | Cl | Me | F | S |
| 15 or, | 2 | Cl | H | Cl | H | S |
| 16 | 2 | Cl | H | 4-Me-Ph | H | S. |

The compounds of the present invention may also be present in the form of pharmaceutically acceptable salts. For use in medicine, the salts of the compounds of this invention refer to non-toxic "pharmaceutically acceptable salts" (Ref. International J. Pharm., 1986, 33, 201–217; J. Pharm. Sci., 1997 (Jan), 66, 1, 1). Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

The compounds according to this invention may have at least one chiral center and thus may exist as enantiomers. In addition, the compounds of the present invention may also possess two or more chiral centers and thus may also exist as diastereomers or as exo or endo isomers. Where the processes for the preparation of the present compounds give rise to a mixture of stereoisomers, these isomers may be separated by conventional techniques such as preparative chromatography. Accordingly, the compounds may be prepared as a racemic mixture or, by either enantiospecific synthesis or resolution, as individual enantiomers. The compounds may, for example, be resolved from a racemic mixture into their component racemates by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The racemic mixture may also be resolved by formation of diastereomeric esters or amides, followed by chromatographic separation and removal of the chiral auxiliary. Alternatively, the compounds may be resolved using a chiral HPLC column. It is to be understood that all such isomers and mixtures thereof are encompassed within the scope of the present invention.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

As used herein, unless otherwise noted, the term "alkyl" whether used alone or as part of a substituent group refers to straight and branched chains having 1 to 8 carbon atoms, or any number within this range. The term "alkoxy" refers to an —O-alkyl substituent group, wherein alkyl is as defined supra. Similarly, the terms "alkenyl" and "alkynyl" refer to straight and branched carbon chains having 2 to 8 carbon atoms, or any number within this range, wherein an alkenyl chain has at least one double bond in the chain and an alkynyl chain has at least one triple bond in the chain.

The term "cycloalkyl" refers to branched or unbranched cyclic aliphatic hydrocarbon chains of 3 to 8 carbon atom members. Examples of such cyclic alkyl rings include cyclopropyl, cyclobutyl, cyclopentyl, cyclohexyl or cycloheptyl.

The bridged bicycloalkyl ring system of the present invention refers to a bridged bicyclic ring system of 4 to 7 carbon atom members (such as a 2.2.2, 2.1.2, 2.1.1 or a 2.2.1 ring system) formed with a nitrogen atom of attachment on the benzodiazepine ring and a carbon atom of attachment on the benzodiazepine ring. The bridge portion of the bridged bicyclic ring system may be formed by attachment with a carbon atom within the bridged bicyclic ring system or the carbon atom of attachment on the benzodiazepine ring.

The term "aryl" refers to a single aromatic ring of 6 carbon members or a bicyclic aromatic ring of 10 carbon members. Examples of such aryl rings include phenyl and naphthyl.

The term "heteroaryl" refers to an aromatic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to two additional nitrogens. In the case of 6 membered rings, the heteroaryl ring may contain from one to three nitrogen atoms. For the case wherein the 6 member ring has three nitrogens, at most two nitrogen atoms are adjacent. Examples of a heteroaryl ring include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl or pyrazinyl.

Optionally, the heteroaryl ring is fused to a benzene ring, a 5 or 6 membered heteroaryl ring (containing one of O, S or N and, optionally, one additional nitrogen), a 5 to 7 membered alicyclic ring or a 5 to 7 membered heterocyclo ring (as defined supra, but absent the option of a further fused ring). Examples of a fused heteroaryl ring include indolyl, isoindolyl, indolinyl, benzofuryl, benzothienyl, indazolyl, benzimidazolyl, benzthiazolyl, benzoxazolyl, benzisoxazolyl, benzothiadiazolyl, benzotriazolyl, quinolizinyl, quinolinyl, isoquinolinyl or quinazolinyl.

The term "arylalkyl" means an alkyl group substituted with an aryl group (e.g., benzyl, phenethyl). Similarly, the term "arylalkoxy" indicates an alkoxy group substituted with an aryl group (e.g., benzyloxy).

As used herein, the term "carboxyl" refers to the linking group —C(O)O— or (when used accordingly) to the substituent —COOH.

Whenever the term "alkyl" or "aryl" or either of their prefix roots appear in a name of a substituent (e.g., arylalkyl, alkylamino) it shall be interpreted as including those limitations given above for "alkyl" and "aryl." Designated numbers of carbon atoms (e.g., $C_1$–$C_6$) shall refer independently to the number of carbon atoms in an alkyl moiety or to the alkyl portion of a larger substituent in which alkyl appears as its prefix root. The amount of substituents attached to a moiety "optionally substituted with one to five substituents" is limited to that amount of open valences on the moiety available for substitution.

In general, under standard nomenclature rules used throughout this disclosure, the terminal portion of the designated side chain is described first followed by the adjacent functionality toward the point of attachment. Thus, for example, a "phenyl $C_1$–$C_6$ alkylamido $C_1$–$C_6$alkyl" substituent refers to a group of the formula:

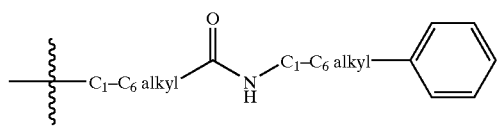

It is intended that the definition of any substituent or variable (e.g., $R_8$) at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

Illustrative of the invention is a pharmaceutical composition comprising a pharmaceutically acceptable carrier and any of the compounds described above. Also illustrative of the invention is a pharmaceutical composition made by mixing any of the compounds described above and a pharmaceutically acceptable carrier. A further illustration of the invention is a process for making a pharmaceutical composition comprising mixing any of the compounds described above and a pharmaceutically acceptable carrier. The present invention also provides pharmaceutical compositions comprising one or more compounds of this invention in association with a pharmaceutically acceptable carrier.

The bridged bicyclic benzodiazepine compounds of the present invention are useful vasopressin receptor antagonists (in particular, inhibitors of $V_{1a}$ and $V_2$) useful for treating vasopressin mediated disorders. Vasopressin mediated disorders include, and are not limited to, conditions with increased vascular resistance, hypertension, congestive heart failure, cardiac insufficiency, coronary vasospasm, cardiac ischemia, liver cirrhosis, renal vasospasm, renal failure, cerebral edema, cerebral ischemia, stroke, thrombosis and water retention.

An embodiment of the invention is a method for treating vasopressin mediated disorders in a subject in need thereof comprising administering to the subject a therapeutically effective amount of any of the compounds or pharmaceutical compositions described above. Also included in the invention is the use of a compound of Formula (I) for the preparation of a medicament for treating vasopressin mediated disorders in a subject in need thereof. The term "treating" as used herein refers to a method for improving, halting, retarding or palliating vasopressin mediated disorder in the subject in need thereof. All such methods of treatment are intended to be within the scope of the present invention.

In accordance with the methods of the present invention, the individual components of the pharmaceutical compositions described herein can also be administered separately at different times during the course of therapy or concurrently in divided or single combination forms. The instant invention is therefore to be understood as embracing all such regimes of simultaneous or alternating treatment and the term "administering" is to be interpreted accordingly.

The term "subject" as used herein, refers to an animal (preferably, a mammal; and, most preferably, a human) who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1–3, edited by Lieberman et al; *Pharmaceutical Dosage Forms: Parenteral Medications*, Volumes 1–2, edited by Avis et al; and *Pharmaceutical Dosage Forms: Disperse Systems*, Volumes 1–2, edited by Lieberman et al; published by Marcel Dekker, Inc.

In preparing a pharmaceutical composition of the present invention in liquid dosage form for oral, topical, inhalation/insufflation and parenteral administration, any of the usual pharmaceutical media or excipients may be employed. Thus, for liquid dosage forms, such as suspensions (i.e. colloids, emulsions and dispersions) and solutions, suitable carriers and additives include but are not limited to pharmaceutically acceptable wetting agents, dispersants, flocculation agents, thickeners, pH control agents (i.e. buffers), osmotic agents, coloring agents, flavors, fragrances, preservatives (i.e. to control microbial growth, etc.) and a liquid vehicle may be employed. Not all of the components listed above will be required for each liquid dosage form.

In solid oral preparations such as, for example, powders, granules, capsules, caplets, gelcaps, pills and tablets (each including immediate release, timed release and sustained release formulations), suitable carriers and additives include but are not limited to diluents, granulating agents, lubricants, binders, glidants, disintegrating agents and the like. Because of their ease of administration, tablets and capsules represent the most advantageous oral dosage unit form, in which case solid pharmaceutical carriers are obviously employed. If desired, tablets may be sugar coated, gelatin coated, film coated or enteric coated by standard techniques.

Preferably these compositions are in unit dosage forms from such as tablets, pills, capsules, powders, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, inhalation or insufflation means. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid pharmaceutical compositions such as tablets, the principal active ingredient is mixed with a pharmaceutical carrier, e.g. conventional tabletting ingredients such as diluents, binders, adhesives, disintegrants, lubricants, antiadherents and glidants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), cross-linked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable glidants include, but are not limited to, talc, cornstarch, silica (i.e. CAB-O-SIL™ silica available from Cabot, SYLOID™ silica available from W.R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active of the present invention, or a pharmaceutically acceptable salt thereof. Generally the preformulation will be formed by one of three common methods: (a) wet granulation, (b) dry granulation and (c)dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agent include pharmaceutical grade lecithins. Suitable flocculating agent include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms, however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in a form suitable for intranasal or inhalation therapy. For such therapy, compounds of the present invention are conveniently delivered in the form of a solution or suspension from a pump spray container that is squeezed or pumped or as an aerosol spray from a pressurized container or a nebulizer (such as, a metered dose inhaler, a dry powder inhaler or other conventional or non-conventional modes or devices for inhalation delivery) using a suitable propellant (such as, dichlorodifluoromethane, trichlorofluoromethane, dichlorotetrafluoroethane, carbon dioxide or other suitable gas). In the case of a pressurized aerosol, the dosage unit may be determined by providing a valve to deliver a metered amount. The pressurized container or nebulizer may contain a solution or suspension of the active compound. Capsules and cartridges (such as, those made from gelatin) for use in an inhaler or insufflator may be formulated containing a powder mix of a compound of the invention and a suitable powder base such as lactose or starch.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

Compounds of the present invention may also be delivered by the use of monoclonal antibodies as individual carriers to which the compound molecules are coupled. The compounds of the present invention may also be coupled with soluble polymers as targetable drug carriers. Such polymers can include, but are not limited to polyvinylpyrrolidone, pyran copolymer, polyhydroxypropylmethacrylamidephenol, polyhydroxyethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, to homopolymers and copolymers (which means polymers containing two or more chemically distinguishable repeating units) of lactide (which includes lactic acid d-, l- and meso lactide), glycolide (including glycolic acid), $\epsilon$-caprolactone, p-dioxanone (1,4-dioxan-2-one), trimethylene carbonate (1,3-dioxan-2-one), alkyl derivatives of trimethylene carbonate, $\delta$-valerolactone, $\beta$-butyrolactone, $\gamma$-butyrolactone, $\epsilon$-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, polyorthoesters, polyacetals, polydihydropyrans, polycyanoacrylates and cross-linked or amphipathic block copolymers of hydrogels and blends thereof.

The therapeutically effective amount of a compound or pharmaceutical composition thereof may be from about 0.001 mg/Kg/dose to about 300 mg/Kg/dose. Preferably, the therapeutically effective amount may be from about 0.001 mg/Kg/dose to about 100 mg/Kg/dose. More preferably, the therapeutically effective amount may be from about 0.001 mg/Kg/dose to about 50 mg/Kg/dose. Most preferably, the therapeutically effective amount may be from about 0.001 mg/Kg/dose to about 30 mg/Kg/dose. Therefore, the therapeutically effective amount of the active ingredient contained per dosage unit (e.g., tablet, capsule, powder, injection, suppository, teaspoonful and the like) as described herein will be in the range of from about 1 mg/day to about 21,000 mg/day for a subject, for example, having an average weight of 70 Kg. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated.

Optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. Advantageously, compounds of the present invention may be administered in a single daily dose or the total daily dosage may be administered in divided doses of two, three or four times daily.

Abbreviations used in the instant specification, particularly the Schemes and Examples, are as follows:
Cpd=compound
DCM=dichloromethane
DIEA=diisopropylethylamine
DMF=N,N-dimethylformamide
DMSO=dimethylsulfoxide
$Et_2O$=diethyl ether
EtOAc=ethyl acetate
EtOH=ethanol
Me=methyl
MeOH=methanol
MPK=milligrams per kilogram
Ph=phenyl
ppt=precipitate(d)
rt=room temperature
sat'd=saturated
TEA=triethylamine Particularly preferred compounds of the present invention include those compounds shown in Table 1. Where it is noted, the letters "R" and "S" indicate the absolute configuration of the carbon atom marked with *(Cahn-Ingold-Prelog rules).

General Synthetic Methods

Representative compounds of the present invention can be synthesized in accordance with the general synthetic methods described below and are illustrated more particularly in the scheme that follows. Since the scheme is an illustration, the invention should not be construed as being limited by the chemical reactions and conditions expressed. The preparation of the various starting materials used in the schemes is well within the skill of persons versed in the art.

Scheme AA is illustrative of a general method for preparing compounds of the invention by reacting Compound AA1 with Compound AA2 in the presence of a base such as DIEA, TEA, pyridine, N-methylmorpholine, polymer-supported tertiary amines or other bases known to those skilled in the art to produce Compound AA3. The nitro group for Compound AA3 was removed to produce the amine Compound AA4. Various acid chloride aryl functionalized groups are reacted with Compound AA4 to produce target Compound AA5.

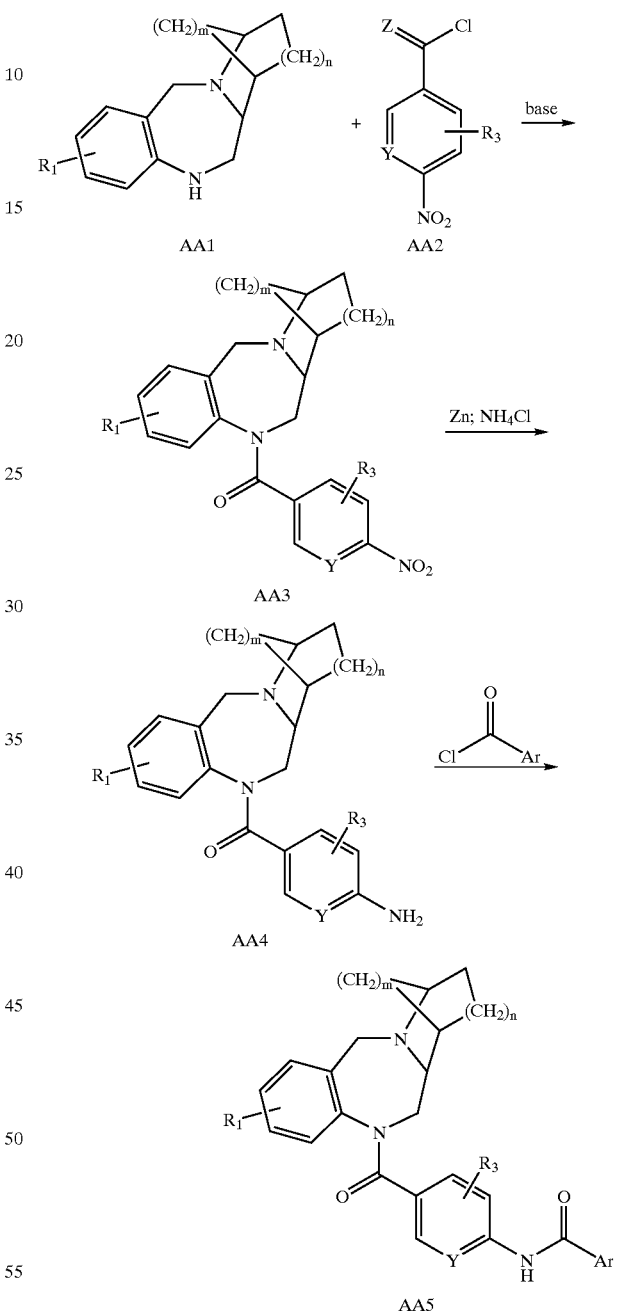

SCHEME AA

Scheme AB is illustrative of an alternative general method for directly preparing target Compound AA5 by reacting Compound AB1 with Compound AB2 in the presence of a base such as DIEA, TEA, pyridine, N-methylmorpholine, polymer-supported tertiary amines or other bases known to those skilled in the art.

SCHEME AB

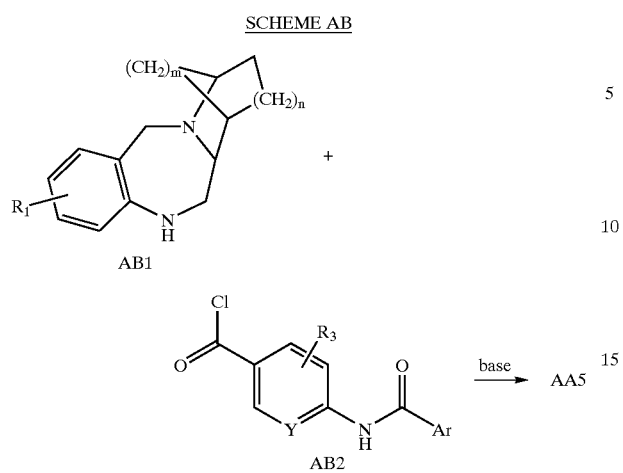

Scheme AC is illustrative of a method for the preparation of an intermediate Compound AC10 for the synthesis of target compounds of Formula (II), wherein m is the integer 2 and n is the integer 1, by reacting Compound AC5 (prepared as described by P. Hamley, A. B. Holmes, A. Kee, T. Ladduwahetty and D. F. Smith in *Synlett.*, 1991, 29–30 for Compound AC1 to AC5) with HBr in acetic acid to produce Compound AC6, which is then reacted with Compound AC7 to produce Compound AC8. Treatment of Compound AC8 with Fe in AcOH provided benzodiazepinone Compound AC9 which was then reduced with LAH to produce the target Compound AC10 (whereby, Compound AC10 is used in place of Compound AA1 in Scheme AA).

SCHEME AC

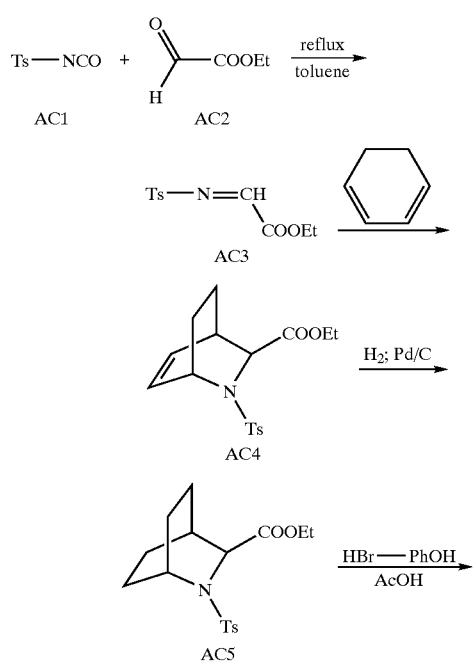

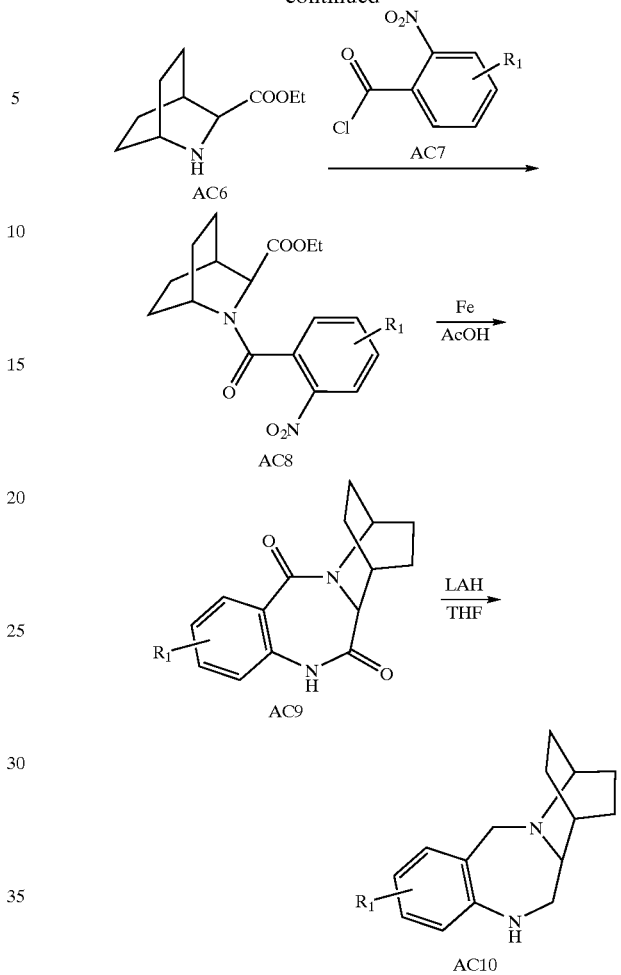

Scheme AD is illustrative of a method for the synthesis of a chiral intermediate Compound AD9 for the preparation of target compounds of Formula (II), wherein m is the integer 2 and n is the integer 1, by reacting Compound AD5 (prepared as described by P. D. Bailey, G. R. Brown, F. Korber, A. Reed and R. D. Wilson in *Tetrahedron: Asymmetry*, 1991, 2(12), 1263–1282) with Compound AD6 to form an amide Compound AD7 which is then cyclized into a lactam Compound AD8. Reduction of the lactam Compound AD8 with LAH in THF resulted in the target compound AD9 (whereby, Compound AD9 is used in place of Compound AA1 in Scheme AA).

SCHEME AD

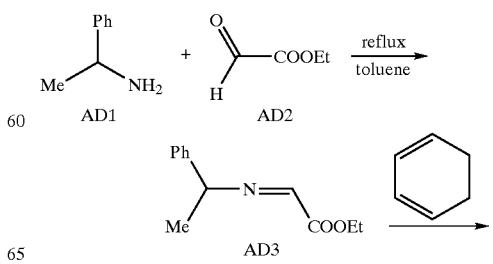

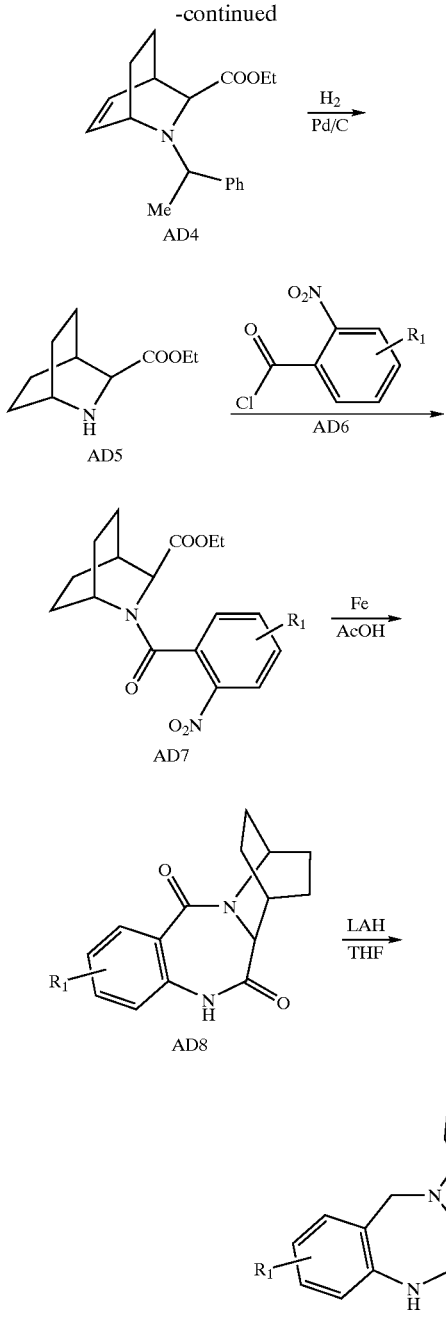

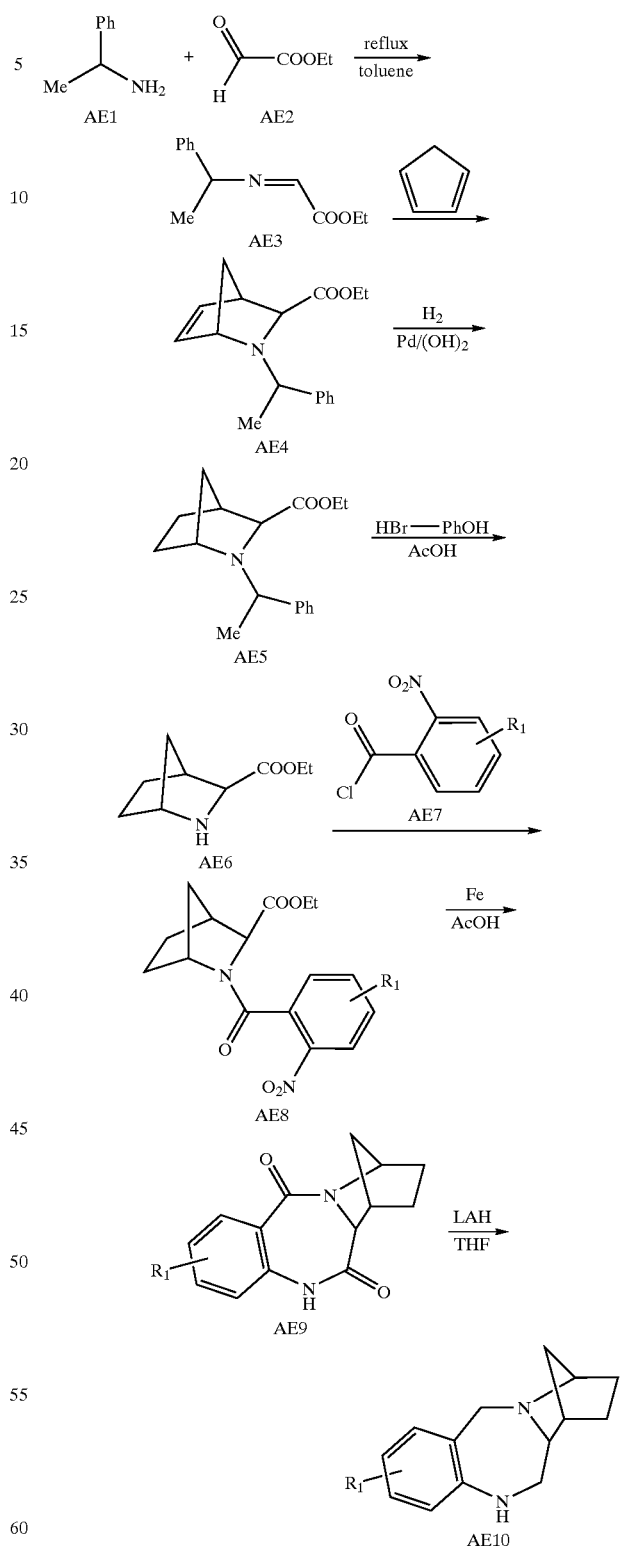

Scheme AE is illustrative of a method for the preparation of an intermediate Compound AE10 for the synthesis of the target compounds of Formula (II) wherein m and n are the integer 1, by reacting Compound AE6 (prepared as described by P. D. Bailey, R. D. Wilson and G. R. Brown in *Tetrahedron Letters*, 1989, 30(48), 6781–6784 for Compound AE1 to AE6) with Compound AE7 to provide Compound AE8, which is then treated with Fe in AcOH to result in the cyclic benzodiazepinone Compound AE9. Reduction of Compound AE9 with LAH in THF provided the intermediate Compound AE10.

Scheme AF is illustrative of a method for the preparation of target compounds of Formula (III) by using the intermediate Compound AF4 (prepared as described by P. Hughes and J. Clardy, *J. Org. Chem.*, 1988, 53, 4793–4796) in place of Compound AE6 in Scheme AE.

SCHEME AF

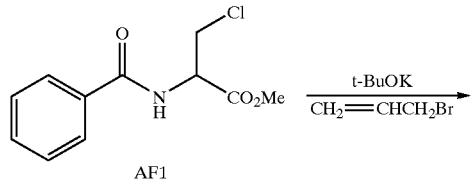

AF1

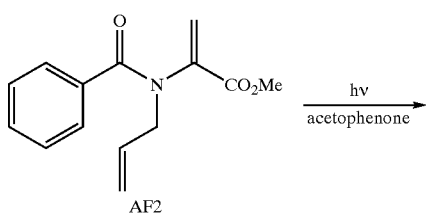

AF2

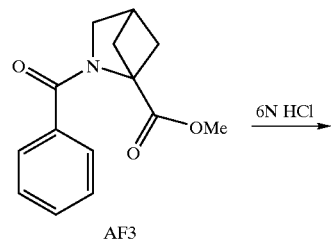

AF3

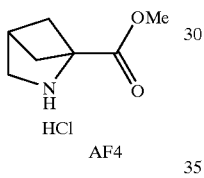

AF4

Scheme AG is illustrative of a method for the preparation of intermediate Compound AG11 for the synthesis of the target compounds of Formula (IV) by hydrolysing Compound AG6 (prepared as described by J. A. Campbell and H. Rapoport, *J. Org. Chem.* 1996, 61, 6313–6325 for Compound AG1 to AG6) in MeOH to produce Compound AG7 which is further reacted with Compound AG8 to produce Compound AF9. Treatment of Compound AG9 with Fe in AcOH produces a benzodiazepinone Compound AG10 which is reduced with LAH in THF to produce the intermediate Compound AG11 (whereby, Compound AG11 is used in place of Compound AA1 in Scheme AA).

SCHEME AG

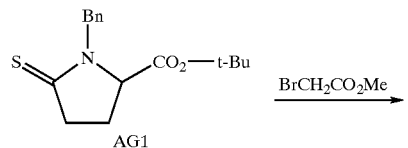

AG1

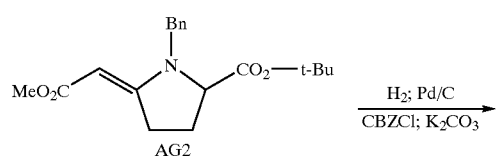

AG2

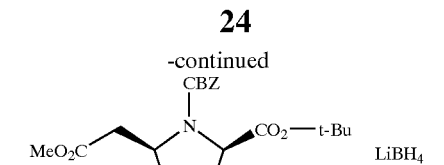

AG3

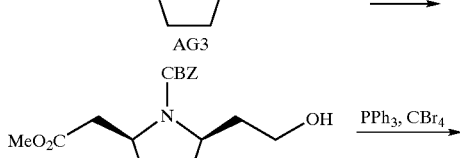

AG4

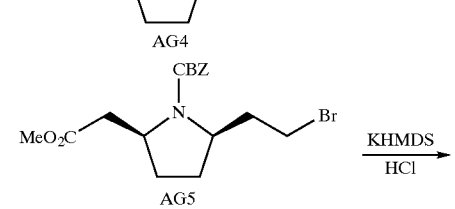

AG5

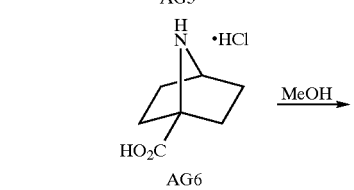

AG6

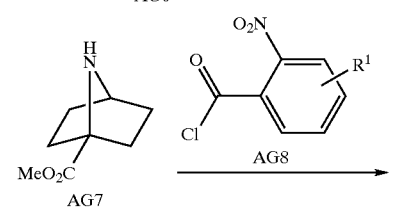

AG7

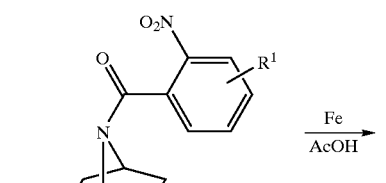

AG9

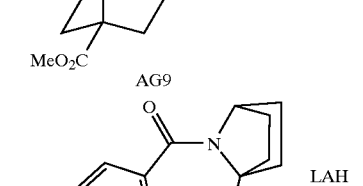

AG10

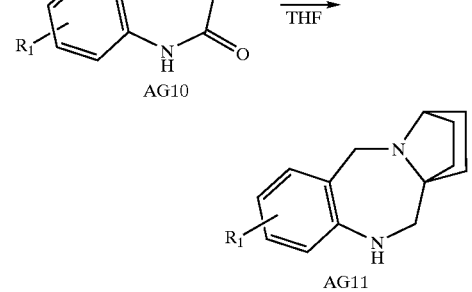

AG11

Specific Synthetic Examples

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The depicted intermediates may also be used in subsequent examples to produce additional compounds of the present invention. No attempt has been made to optimize the yields obtained in any of the reactions. One skilled in the art would know how to increase such yields through routine variations in reaction times, temperatures, solvents and/or reagents.

Reagents were purchased from commercial sources. High field $^1$H NMR spectra were recorded on a Bruker AC-360 spectrometer at 360 MHz, and coupling constants are given in Hertz. Melting points were determined on a Mel-Temp II melting point apparatus and are uncorrected. Microanalyses are expressed in percentage by weight of each element per total molecular weight. In all cases the products were obtained as a salt by treatment of the free base with HCl in ether. Nuclear magnetic resonance (NMR) spectra for hydrogen atoms were measured in the indicated solvent with tetramethylsilane (TMS) as the internal standard on a Bruker AM-360 (360 MHz) spectrometer. The values are expressed in parts per million down field from TMS. The mass spectra (MS) were determined on a Micromass Platform LC spectrometer using electrospray techniques as (ESI) m/z (M+H$^+$). Stereoisomeric compounds may be characterized as racemic mixtures or as separate diastereomers and enantiomers thereof using X-ray crystallography and other methods known to one skilled in the art. Unless otherwise noted, the materials used in the examples were obtained from readily available commercial suppliers or synthesized by standard methods known to anyone skilled in the art of chemical synthesis. Substituent groups, which vary between examples, are hydrogen unless otherwise noted. Representative names for compounds of the present invention were derived using the ACD/LABS SOFTWARE™ Index Name Pro Version 4.5 software nomenclature program provided by Advanced Chemistry Development, Inc., Toronto, Ontario, Canada.

EXAMPLE 1

N-[4-[(6,6a,7,8,9,10-hexahydro-7,10-ethanopyrido [2,1-c][1,4]benzodiazepin-5(12H)-yl)carbonyl]-3-chlorophenyl]-[1,1'-biphenyl]-2-carboxamide (Compound 2)

Following the method of Scheme AC, a mixture of 15.25 g of p-toluenesulfonyl isocyanate and 20 mL 50% solution of ethyl glyoxalate in toluene with 50 mL of toluene was heated under reflux for 36 h, then 10 mL of 1,3-cyclohexadiene were added as one portion. The reaction was heated for an additional 8 h and cooled down. The product was ppt from toluene, and was recrystallized from hexane ethyl acetate providing 13.0 g (50% yield) of the cycloadduct (see Scheme AC, Compound AC4) as white crystals: mp. 140–142° C.). The cycloadduct was mixed with 200 mg of 10% Pd/C, 150 mL of ethyl acetate and 150 mL of ethanol and was hydrogenated for 24 h at rt. The reaction mixture was filtered through celite and evaporated. The residual material was recrystallized from hexane ethyl acetate providing 12.0 g of the tosylate as white crystals (see Compound AC5, Scheme AC). NMR (CDCl$_3$) 7.88 (d, J=8, 2H), 7.28 (d, J=8, 2H), 4.34 (d, J=2,1H), 4.22 (q, J=6, 2H), 3.62 (m, 1H), 2.42 (s, 3H), 2.22 (m, 1H), 2.00 (m, 1H), 1.80 (m, 1H), 1.70–1.30 (m, 6H), 1.28 (t, J=7, 3H). The tosylate (2.0 g) was dissolved in 50 mL EtOAc containing phenol (6.0 g), then 100 mL of 30% solution of HBr in AcOH was added dropwise. The reaction was allowed to stir 48 h, then EtOAc and most of the AcOH was evaporated under reduced pressure. The residue was dissolved in water, neutralized with Na$_2$CO$_3$ and extracted with Et$_2$O. The organic solution was saturated using HCl and evaporated providing 0.85 g of a yellow solidified oil (see Compound AC6, Scheme AC).

A solution of the oil in 10 mL DCM, containing 0.2 g of Et$_3$N, was treated with 0.79 g of 2-nitrobenzoyl chloride (see Compound AC7, Scheme AC; where R$_1$=H). The reaction was allowed to stir for 4 h, washed with sat'd sodium bicarbonate, dried (MgSO$_4$) and evaporated, providing 1.03 g (80%) of a yellow oil (see Compound AC8, Scheme AC). MS m/e 333.1 (MH$^+$). A 50 mL flask with reflux condenser was loaded with 1.0 g (0.003 M) of the oil, 150 mg of iron filings and 30 mL of AcOH. The reaction was refluxed for 4 h, was separated from non-reacted iron and AcOH was evaporated off under reduced pressure. The residue was mixed with 150 mL of water, after 20 min of stirring a white solid ppt was filtered, washed with large amount of cold water and dried in a vacuum oven providing the dione intermediate 6a,7,9,10-tetrahydro-7,10-ethanopyrido[2,1-c][1,4]benzodiazepine-6,12(5H,8H)-dione (see Compound AC9, Scheme AC) as white solid (0.57 g, 0.0023 M, 75%). $^1$H NMR (CDCl$_3$): 8.13 (s, 1H), 8.04 (d, J=7, 1H), 7.47 (t, J=6, 1H), 7.27 (t, J=7, 1H), 6.95 (d, J=8, 1H), 4.73 (d, J=3, 1H), 3.87 (d, J=3, 1H), 2.6 (m, 1H), 2.29 (s, 1H), 2.0 (m, 1H), 1.9–1.4 (m, 6H). MS m/e 257 (MH$^+$).

A solution of 0.57 g of the dione intermediate in 30 mL of dry THF was treated with 7 mL of 1 M solution of LAH in THF (3 eq.). The reaction was allowed to stir 1 h and was refluxed for 4 h. After cooling down, the reaction was quenched with 0.1 mL H$_2$O, 0.3 mL 1N NaOH and 0.1 mL H$_2$O, diluted with 50 mL Et$_2$O, filtered through celite and evaporated, providing the benzodiazepine intermediate 5,6,6a,7,8,9,10,12-octahydro-7,10-ethanopyrido[2,1-c][1,4]benzodiazepine (see Compound AC10, Scheme AC) as yellow solidified oil (0.35 g, 70%). $^1$H NMR (CDCl$_3$): 7.05 (m, 2H), 6.72 (m, 2H), 3.9 (broad s, 1H), 3.79 (d, J=14, 1H), 3.69 (d, J=14, 1H), 3.16 (m, 1H), 2.98 (m, 1H), 2.75 (s, 1H), 2.62 (d, J=9, 1H), 2.0–1.2 (m, 9H). MS m/e 230 (MH$^+$).

A solution of the ethanopyrido-benzodiazepine intermediate (see Compound AA1, Scheme AA, where R$_1$=H, m=2 and n=1)(0.35 g, 0.0015 M) and Et$_3$N (0.2 g) in 20 mL DCM was treated with 0.4 g of 2-chloro-4-nitro benzoyl chloride (see Compound AA2, Scheme AA, where Y=CH, Z=O and R$_3$=Cl). The solution was allowed to stir for 3 h at rt, washed with saturated sodium bicarbonate and solvent evaporated. The residue was purified by column chromatography (silica, hexane-EtOAc 1:1) providing a yellow solidified foam (see Compound AA3, Scheme AA, where R$_1$=H, m=2, n=1, Y=CH and R$_3$=Cl) (0.38 g, 60% yield). MS m/e 378 (MH$^+$).

The yellow solidified foam (0.38 g, 0.0009 M) was mixed with Zn (0.6 g), NH$_4$Cl (0.3 g) and 100 mL MeOH and was refluxed for 2 h, filtered through celite and the filtrate was evaporated. The residue was dissolved in 1 N HCl, neutralized by sodium bicarbonate and extracted by EtOAc. The organic extract was dried over MgSO$_4$ and evaporated. The residue was purified by column chromatography (silica, EtOAc) providing an amide intermediate (see Compound AA4, Scheme AA) as a white solidified foam (0.28 g, 80% yield). MS m/e 348 (MH$^+$).

A mixture of 2-biphenyl benzoic acid (see the Ar substituted acid chloride, where ClCO—Ar=ClCO-1,1'-biphenyl, Scheme AA) (0.175 g), DMF (50 μL) and 10 mL DCM was treated with 2 mL of a 2N solution of oxalyl chloride in DCM, allowed to stir for 2 h at rt and then the solvent was evaporated. The residue was dissolved in 5 mL dry DCM and added to a solution of the amide intermediate (0.28 g, 0.0007 M) in 200 μL of TEA. The reaction was allowed to stir for 5 h, washed with saturated sodium bicarbonate and then the solvent was evaporated. The residue was purified by column chromatography (silica, ethyl acetate). The fractions containing pure Compound 2 were then evaporated, dissolved in a small amount of DCM and a 1N solution of HCl in Et$_2$O was added. The hydrochloride salt of Compound 2 was pptd, filtered and dried in a vacuum oven providing 0.350 g (81%, 0.00057 M) of a white solid material. MS m/e 562 (MH$^+$). Anal. calcd. for C$_{35}$H$_{33}$N$_3$O$_2$Cl.HCl.H$_2$O (615.2): C, 66.24; H, 5.88; N, 6.62; Cl, 11.17. Found: C, 66.19; H, 5.91; N, 6.44; Cl, 11.31; KF, 4.85.

Following the procedure of Example 1 and substituting the appropriate starting materials, compounds and reagents, the following compounds of the invention were also prepared:

| Cpd | Name | MS m/e (MH$^+$) |
| --- | --- | --- |
| (1) | N-[4-[(6,6a,7,8,9,10-hexahydro-7,10-ethano-pyrido[2,1-c][1,4]benzodiazepin-5(12H)-yl)carbonyl]phenyl]-[1,1'-biphenyl]-2-carboxamide | 528 |

Example 2

N-[4-[[(6aS)-6,6a,7,8,9,10-hexahydro-7,10-methanopyrido[2,1-c][1,4]benzodiazepin-5(12H)-yl]carbonyl]-3-chlorophenyl]-[1,1'-biphenyl]-2-carboxamide (Compound 4)

(R)-(+)-α-methylbenzylamine (see Compound AD1, Scheme AD) (24.2 g, 0.2 M) was mixed with 40 mL of a 50% solution of ethyl glyoxalate (see Compound AD2, Scheme AD) in toluene (0.2 M) and the toluene was removed in vacuo. A solution of the resulting residue (see Compound AD3, Scheme AD) in 150 mL of DMF, 50 mL of freshly distilled cyclopentadiene, 110 μL of water and 14 mL of TFA was stirred at rt for 24 hr. The mixture was quenched with 50 mL of 1N NaHCO$_3$ (aq) and diluted with 400 mL of brine. The solution was then extracted with ethyl acetate and the organic fraction was dried (MgSO$_4$) and concentrated. The residue was purified by column chromatography (silica gel; EtOAc/hexane 1:9) and isolated as a yellow oil (see Compound AD4, exo-(R)-isomer, Scheme AD) (21 g, 40%). A mixture of 21 g of the yellow oil and 200 mg of Pd(OH)$_2$ in EtOH was hydrogenated for 24 hr and filtered through a celite pad. The filtrate was concentrated in vacuo, treated with 1N HCl (aq) in ether and concentrated. The residue was crystallized from DCM-ether to afford the product (see Compound AD5, Scheme AD) as white crystals (12.0 g). $^1$H NMR (D$_2$O) 4.70 (s, 2H), 4.47 (q, J=7, 2H), 4.24 (s, 1H), 2.95 (m, 1H), 1.9–1.6 (m, 7H), 1.20 (t, J=7, 3H).

A solution of the white crystals (0.205 g), 10 mL DCM, containing 0.2 g of Et$_3$N was treated with 0.2 g of 2-nitrobenzoyl chloride (see Compound AD6, Scheme AD; where R$_1$=H). The reaction was allowed to stir for 4 h. The product was washed with saturated sodium bicarbonate, dried (MgSO$_4$) and solvent evaporated off. The residue was purified by column chromatography (silica, hexane:EtOAc 1:1), providing the product as a yellow oil (0.250 g, 78%) (see Compound AD7, Scheme AD). A 50 mL flask with reflux condenser was loaded with 0.5 g (0.00156 M) of the yellow oil, 150 mg of iron filings and 30 mL of AcOH. The reaction was refluxed for 4 h, was separated from non-reacted iron and AcOH was evaporated under reduced pressure. The residue was mixed with 150 mL of water, after 20 min of stirring, a white solid was precipitated, filtered, washed with large amount of cold water and dried in a vacuum oven providing the product (see Compound AD8, Scheme AD) as a white solid (0.264 g, 0.0011 M, 70%). $^1$H NMR (CDCl$_3$): 8.36 (s, 1H), 8.07 (d, J=7, 1H), 4.45 (m, 1H), 7.25 (m, 1H), 6.96 (d, J=8, 1H), 4.76 (s, 1H), 3.58 (s, 1H), 3.15 (s, 1H), 2.0–1.3 (m, 6H).

A solution of 0.242 g of the white solid in 30 mL of dry THF was treated with 3 mL of a 1 M solution of LAH in THF (3 eq.). The reaction was allowed to stir for 1 h and was refluxed 4 h. After cooling down, the reaction was quenched with 0.1 mL H$_2$O, 0.3 mL 1N NaOH and 0.1 mL H$_2$O, diluted with 50 mL Et$_2$O, filtered through celite and evaporated, providing as methanopyrido-benzodiazepine intermediate product (see Compound AD9, Scheme AD) as yellow oil (0.25 g, 87%). MS m/e 229 (MH$^+$). The synthesis of Compound 4 (as the S-enantiomer; see Compound AA5, Scheme AA; where R$_1$=H, m=1, n=1, Y=CH, R$_3$=Cl and Ar=1,1'-biphenyl) was performed according to the method described in Example 1, replacing the ethanopyrido-benzodiazepine intermediate with the methanopyrido-benzodiazepine intermediate product produced herein. Anal. calcd. for C$_{34}$H$_{30}$N$_3$O$_2$Cl.HCl.H$_2$O (601.19): C, 67.77; H, 5.52; N, 6.92; Cl, 11.77. Found: C, 68.06; H, 5.24; N, 6.97; Cl, 11.55. MS m/e 548 (MH$^+$).

Following the procedure of Example 2 and substituting the appropriate starting materials, compounds and reagents, the following compounds of the invention were also prepared:

| Cpd | Name | MS m/e (MH$^+$) |
| --- | --- | --- |
| (3) | N-[4-[[(6aS)-6,6a,7,8,9,10-hexahydro-7,10-methanopyrido[2,1-c][1,4]benzodiazepin-5(12H)-yl]carbonyl]-3-chlorophenyl]-[1,1'-biphenyl]-2-carboxamide | 548 |

Example 3

N-[4-[[(6aR)-6,6a,7,8,9,10-hexahydro-7,10-methanopyrido[2,1-c][1,4]benzodiazepin-5(12H)-yl]carbonyl]-3-chlorophenyl]-[1,1'-biphenyl]-2-carboxamide (Compound 5)

The R-enantiomer of Compound 4 was prepared from (S)-(+)-α-methylbenzylamine according to the method described in Example 2. Anal. calcd. for C$_{34}$H$_{30}$N$_3$O$_2$.HCl.H$_2$O (601.19): C, 67.77; H, 5.52; N, 6.92; Cl, 11.77. Found: C, 67.90; H, 5.36; N, 6.91; Cl, 11.99. MS m/e 548 (MH$^+$).

Example 4

N-[4-[[(6aS)-2-chloro-6,6a,7,8,9,10-hexahydro-7,10-methanopyrido[2,1-c][1,4]benzodiazepin-5(12H)-yl]carbonyl]phenyl]-4'-methyl-[1,1'-biphenyl]-2-carboxamide (Compound 6)

The methanopyrido-benzodiazepine intermediate product used to prepare Compound 6, replacing the ethanopyrido-benzodiazepine intermediate in Example 1, was prepared according to the method of Example 2 by substituting the appropriate starting materials, compounds and reagents.

The benzodiazepinone intermediate (see Compound AD8, Scheme AD; where R$_1$=Cl) was obtained as a white solid. $^1$H NMR (CDCl$_3$): 8.28 (s, 1H), 8.05 (s, 1H), 7.42 (d, J=8, 1H), 6.93 (d, J=8, 1H), 4.74 (s, 1H), 3.57 (s, 1H), 3.16 (s, 1H), 2.0–1.3 (m, 6H). The benzodiazepine HCl salt (see Compound AD9, Scheme AD) was then crystallized from the white solid. $^1$H NMR (D$_2$O):7.05 (d, J=8, 1H), 6.95 (s, 1H), 6.52 (d, J=8, 1H), 5.10 (d, J=14, 1H), 4.70 (s, 2H), 4.1–3.9 m, 4H), 3.15 (d, J=16, 1H), 2.48 (broad s, 1H), 2.09 (d, J=12, 1H), 1.9–1.2 (m, 5H). MS m/e 249 (MH$^+$). The synthesis of Compound 6 (as the S-enantiomer; see Compound AA5, Scheme AA; where R$_1$=Cl, m=1, n=1, Y=CH, R$_3$=H and Ar=4'-methyl-1,1'-biphenyl), was performed according to the method of Example 1. Anal. calcd. for C$_{34}$H$_{32}$ClN$_3$O$_2$.HCl.2H$_2$O (634.59): C, 66.24; H, 5.88; N, 6.62; Cl, 11.17. Found: C, 66.07; H, 6.28; N, 6.75; Cl, 11.00; KF 5.36. MS m/e 562 (MH$^+$).

Following the procedure of Example 4 and substituting the appropriate starting materials, compounds and reagents, the following compounds of the invention were also prepared:

| Cpd | Name | MS m/e (MH$^+$) |
|---|---|---|
| (7) | N-[4-[[(6aS)-6,6a,7,8,9,10-hexahydro-7,10-methanopyrido[2,1-c][1,4]benzodiazepin-5(12H)-yl]carbonyl]-3-chlorophenyl]-4'-methyl-[1,1'-biphenyl]-2-carboxamide | 562 |
| (8) | N-[4-[[(6aS)-2-chloro-6,6a,7,8,9,10-hexahydro-7,10-methanopyrido[2,1-c][1,4]benzodiazepin-5(12H)-yl]carbonyl]-3-chlorophenyl]-4'-methyl-[1,1'-biphenyl]-2-carboxamide | 596 |
| (9) | N-[4-[[(6aS)-2-chloro-6,6a,7,8,9,10-hexahydro-7,10-methanopyrido[2,1-c][1,4]benzodiazepin-5(12H)-yl]carbonyl]phenyl]-4'-fluoro-[1,1'-biphenyl]-2-carboxamide | 566 |
| (10) | N-[4-[[(6aS)-2-chloro-6,6a,7,8,9,10-hexahydro-7,10-methanopyrido[2,1-c][1,4]benzodiazepin-5(12H)-yl]carbonyl]phenyl]-2-fluoro-benzamide | 490 |
| (11) | N-[4-[[(6aS)-2-chloro-6,6a,7,8,9,10-hexahydro-7,10-methanopyrido[2,1-c][1,4]benzodiazepin-5(12H)-yl]carbonyl]phenyl]-2-chloro-benzamide | 506 |
| (12) | N-[4-[[(6aS)-2-chloro-6,6a,7,8,9,10-hexahydro-7,10-methanopyrido[2,1-c][1,4]benzodiazepin-5(12H)-yl]carbonyl]-3-chlorophenyl]-2-(trifluoromethyl)-benzamide | 540 |

Example 5

(R)-(+)-α-methylbenzylamine (see Compound AD1, Scheme AD) (12.1 g), was mixed with 20 mL 50% solution of ethyl glyoxalate (see Compound AD2, Scheme AD) in toluene. The reaction was stirred for 30 min and evaporated in vacuo to provide a yellow viscous oil (see Compound AD3, Scheme AD). The oil was dissolved in 300 mL of dry DCM and cooled down in dry ice/acetone bath (N$_2$ atmosphere). TFA (6 mL, 8.81 g) was added dropwise followed by BF$_3$ diethyl etherate (12 mL, 13.5 g). The reaction mixture was stirred for 10 min and 1,3-cyclohexadiene (15 mL) was added dropwise over 30 min period. The reaction was kept in the cooling bath for 3 h, warmed up to rt and stirred for 24 h. The resulting mixture was washed with NaHCO$_3$ 10% aq and evaporated. The residue was subjected to column chromatography (silica, hexane/EtOAc 9:1) providing a colorless oil (see Compound AD4, Scheme AD) (15.1 g). $^1$H NMR (CDCl$_3$) 7.49–7.40 (m, 2H), 7.27–7.15 (m, 3H), 6.39 (t, J=7, 1H), 6.26 (t, J=5, 1H), 4.20 (q, J=7, 2H), 3.61 (m, 1H), 3.60 (q, J=3, 1H), 2.89 (m, 1H), 2.73 (m, 1H), 2.1–2.0 (m, 1H), 1.63–1.58 (m, 1H), 1.59 (d, J=3, 3H), 1.11 (t, J=7, 3H), 1.3–1.0 (m, 2H).

A suspension of the colorless oil (see Compound AD4, Scheme AD) (15.1 g) with 10% Pd/carbon (200 mg) in 200 mL of EtOH was hydrogenated for 24 h (30 psi, rt). The reaction mixture was filtered through celite and concentrated in vacuo providing a colorless oil (see Compound AD5, Scheme AD) (11.5 g).

Following the procedure of Example 5 and substituting the product in Example 1 (analogously, see Compound AC6, Scheme AC), the following compounds of the invention were also prepared:

| Cpd | Name | MS m/e (MH$^+$) |
|---|---|---|
| (13) | N-[4-[[(6aS)-6,6a,7,8,9,10-hexahydro-7,10-ethanopyrido[2,1-c][1,4]benzodiazepin-5(12H)-yl]carbonyl]-3-chlorophenyl]-[1,1'-biphenyl]-2-carboxamide | 562 |
| (14) | N-[4-[[(6aS)-6,6a,7,8,9,10-hexahydro-7,10-ethanopyrido[2,1-c][1,4]benzodiazepin-5(12H)-yl]carbonyl]-3-chlorophenyl]-5-fluoro-2-methyl-benzamide | 518 |
| (15) | N-[4-[[(6aS)-2-chloro-6,6a,7,8,9,10-hexahydro-7,10-ethanopyrido[2,1-c][1,4]benzodiazepin-5(12H)-yl]carbonyl]phenyl]-2-chloro-benzamide | 520 |
| (16) | N-[4-[[(6aS)-2-chloro-6,6a,7,8,9,10-hexahydro-7,10-ethanopyrido[2,1-c][1,4]benzodiazepin-5(12H)-yl]carbonyl]phenyl]-4'-methyl-[1,1'-biphenyl]-2-carboxamide | 576 |

Biological Examples

The utility of the compounds to treat vasopressin mediated disorders, particularly vasopressin disorders mediated by inhibition of the $V_{1a}$ or $V_2$ receptor, was determined using the following procedures.

Example 1

In Vitro Recombinant Vasopressin Receptor Binding Assay

Compounds were assessed for their ability to displace $^3$H-arginine vasopressin from the human $V_{1a}$ or $V_2$ receptor in HEK-293 cells. Assay buffer is 50 mM Tris-Cl, 5 mM MgCl$_2$, 0.1% BSA (pH 7.5) containing 5 µg/mL of aprotinin, leupeptin, pepstatin, 50 µg/mL bacitracin, and 1 mM Pefabloc. $^3$H-vasopressin is $^3$H-arginine-8-vasopressin (68.5 Ci/mmol, final concentration in assay is 0.65–0.75 nM). Into wells of 96-well round bottom polypropylene plates were added buffer, test compound, membrane (containing cloned human $V_{1a}$ or $V_2$ receptor) and $^3$H-vasopressin. The reaction plates were allowed to sit at room temperature for one hour. The samples were filtered through Unifilter GF/C plates (presoaked in 0.3 polyethyleneimine). The plates were washed 5 times with cold physiological saline containing 0.05% Tween 20. After drying, the bottom of the filter plates were sealed and 0.025 mL of Microscint-20 was added to each filter. The top of the plate was sealed, and the plate was counted. Non-specific binding was determined by the addition of 1.25 µM arginine-8-vasopressin into the wells and is shown in Table 2.

TABLE 2

| | Vasopressin Binding | |
|---|---|---|
| Cpd | $V_{1a}$ IC$_{50}$ (nM) | $V_2$ IC$_{50}$ (nM) |
| 1 | 46% (@ 0.1 µM) | 6 |
| 2 | 30% (@ 0.1 µM) | 4 |
| 3 | 29% (@ 0.1 µM) | 15 |
| 4 | 24 | 4 |
| 5 | 7% (@ 0.1 µM) | 15 |

TABLE 2-continued

| | Vasopressin Binding | |
|---|---|---|
| Cpd | $V_{1a}$ $IC_{50}$ (nM) | $V_2$ $IC_{50}$ (nM) |
| 6 | 24 | 5 |
| 7 | 35 | 3 |
| 8 | 46% (@ 0.1 μM) | 53% (@ 0.1 μM) |
| 9 | 68 | 26 |
| 10 | 5 | 10 |
| 11 | 4 | 7 |
| 12 | 10 | 15 |
| 13 | 34% (@ 0.2 μM) | 24 |
| 14 | 15% (@ 0.2 μM) | 19 |
| 15 | 13 | 35 |
| 16 | 59 | 72 |

Example 2

Diuresis Study

The acute diuretic effect of compounds of the invention after oral administration was tested according to the procedure described herein.

Mature male Sprague Dawley rats, 200–300 gms, from Charles River Labs Inc. were housed one rat per cage, in a rodent room. Room temperature was maintained at 64–79° C. and humidity at 30–70%. Room lighting was on a 12 hrs light/12 hrs dark cycle. Rats were fed laboratory rodent diet, #5001 (supplied from Purina Mills, St.Louis, Mo. via W. F. Fisher, Bound Brook, N.J.).

Four different concentrations of test compound were prepared. For each dose, compound was prepared as a uniform suspension in 0.5% methylcellulose vehicle using a water bath sonicator to ensure uniform suspension and dosed in a volume of 2 ml/kg.

All animals were fasted for 18 hours and weights were taken and recorded for each animal. Animals were dosed orally with drug via gavage needle. After oral dosing, animals were placed into metabolism racks for 4 hours. The urine was collected and the volume measured. Aliquots of 0.5 mL were stored at 4° C. for later analysis.

Table 3 shows the effect of instant compounds on urine volume and osmolality in conscious hydrated male rats. Each value represents the mean±SE. *Data has a p value of <0.05 versus vehicle using Dunnett's Multiple Comparison Test. **Data has a p value of <0.01 versus vehicle. [a]Number of animals in parentheses represent the number of animals providing osmolality values (if different than the number of animals providing urine volume values).

TABLE 3

| Dose (mg/Kg) | No. Animals[a] | Urine Volume (mL) | Urine Osmolality (mOsm/kg) |
|---|---|---|---|
| Compound 4 | | | |
| Vehicle | 10 (9) | 1.1 ± 0.2 | 663 ± 62 |
| 0.3 | 9 | 2.5 ± 0.3 | 444 ± 79* |
| 1.0 | 10 | 6.0 ± 0.7* | 299 ± 34* |
| 3.0 | 10 | 15.1 ± 1.4* | 180 ± 9* |
| 10 | 10 | 29.9 ± 2.0* | 138 ± 11* |
| Compound 5 | | | |
| Vehicle | 10 (8) | 0.6 ± 0.1 | 892 ± 70 |
| 0.3 | 9 | 1.4 ± 0.1* | 408 ± 37* |
| 1.0 | 10 | 3.4 ± 0.4* | 303 ± 29* |
| 3.0 | 10 | 9.4 ± 1.1* | 238 ± 18* |
| 10 | 10 | 19.5 ± 1.4* | 172 ± 9* |

TABLE 3-continued

| Dose (mg/Kg) | No. Animals[a] | Urine Volume (mL) | Urine Osmolality (mOsm/kg) |
|---|---|---|---|
| Compound 6 | | | |
| Vehicle | 10 | 2.3 ± 0.3 | 441 ± 30 |
| 1.0 | 10 | 2.9 ± 0.2 | 387 ± 15 |
| 3.0 | 10 | 5.8 ± 0.5** | 226 ± 9** |
| 10 | 10 | 17.8 ± 1.3** | 159 ± 9** |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula (I):

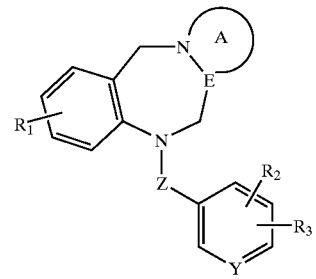

Formula (I)

wherein

A is a bridged bicycloalkyl ring system of 4 to 7 carbon atoms formed with a nitrogen atom of attachment and E;

E is selected from the group consisting of a). a —C— atom of attachment bonded to the nitrogen atom of attachment and two carbon atoms of the bridged bicycloalkyl ring system and b). a —CH— atom of attachment bonded to the nitrogen atom of attachment and one carbon atom of the bridged bicycloalkyl ring system;

$R_1$ is one to four substituents independently selected from the group consisting of hydrogen, $C_{1-8}$alkyl (optionally substituted on a terminal carbon atom with a substituent selected from the group consisting of aryl, heteroaryl, hydroxy and (halo)$_{1-3}$), $C_{1-8}$alkoxy (optionally substituted on a terminal carbon atom with a substituent selected from the group consisting of hydroxy and (halo)$_{1-3}$), $C_{2-8}$alkenyl, $C_{2-8}$alkynyl, aryl, heteroaryl, halogen, and hydroxy;

$R_2$ is selected from the group consisting of —NR$_4$COAr, —NR$_4$CO-heteroaryl, —NR$_4$Ar, —CH=CH—Ar, —CF=CH—Ar, —CH=CF—Ar, —CCl=CH—Ar, —CH=CCl—Ar, —CH=CH-heteroaryl, —CF=CH-heteroaryl, —CH=CF-heteroaryl, —CCl=CH-heteroaryl, —CH=CCl-heteroaryl, —OCH$_2$—Ar, —OCH$_2$-heteroaryl, —SCH$_2$—Ar and —NR$_4$CH$_2$Ar;

Ar is selected from the group consisting of aryl and heteroaryl optionally substituted with one to five substituents independently selected from the group consisting of $C_{1-8}$alkyl (optionally substituted on a terminal carbon atom with a substituent selected from the group consisting of aryl, heteroaryl, amino (optionally substituted with one to two substituents selected from $C_{1-8}$alkyl), hydroxy and (halo)$_{1-3}$), $C_{1-8}$alkoxy (optionally substituted on a terminal carbon atom with a substituent selected from the group consisting of aryl, hydroxy and (halo)$_{1-3}$), aryl, heteroaryl, carboxyl, amino (optionally substituted with one to two substituents selected from $C_{1-8}$ alkyl), $C_{1-8}$ alkylsulfonyl, $C_{1-8}$ alkylsulfinyl, thio (substituted with a substituent selected from the group consisting of $C_{1-8}$alkyl and (halo)$_{1-3}$($C_{1-8}$)alkyl), cyano, halogen, hydroxy and nitro;

wherein aryl, heteroaryl and the aryl and heteroaryl portions of any of the foregoing substituents are optionally substituted with one to four substituents independently selected from the group consisting of $C_{1-8}$alkyl (optionally substituted on a terminal carbon atom with a substituent selected from the group consisting of amino (optionally substituted with one to two substituents selected from $C_{1-8}$alkyl), hydroxy and (halo)$_{1-3}$), $C_{1-8}$alkoxy (optionally substituted on a terminal carbon atom with a substituent selected from the group consisting of hydroxy and (halo)$_{1-3}$), carboxyl, amino (optionally substituted with one to two substituents selected from $C_{1-8}$ alkyl), $C_{1-8}$ alkylsulfonyl, $C_{1-8}$ alkylsulfinyl, $C_{1-8}$ alkylthio, cyano, halogen, hydroxy, and nitro;

$R_3$ is one to three substituents independently selected from the group consisting of hydrogen, $C_{1-8}$alkyl (optionally substituted on a terminal carbon atom with a substituent selected from the group consisting of amino (optionally substituted with one to two substituents selected from $C_{1-8}$alkyl), hydroxy and (halo)$_{1-3}$), $C_{1-8}$alkoxy (optionally substituted on a terminal carbon atom with a substituent selected from the group consisting of hydroxy and (halo)$_{1-3}$), amino (optionally substituted with one to two substituents selected from $C_{1-8}$ alkyl), halogen, and hydroxy;

$R_4$ is hydrogen or $C_{1-8}$ alkyl;

Y is CH or N; and,

Z is $CH_2$, CH, —C(O)—, or —$SO_2$—;

heteroaryl is an aromatic ring of 5 or 6 members wherein the ring consists of carbon atoms and 1–3 heteroatoms selected from the group consisting of nitrogen, oxygen, and sulfur, said heteroaryl optionally fused to: 1) a benzene ring; 2) a 5 or 6 membered heteroaryl ring containing one of O, S or N and, optionally, one additional N; 3) a 5 to 7 membered alicyclic ring; or 4) a 5 to 7 membered heterocyclo ring, said ring being not further fused;

or pharmaceutically acceptable salts, racemic mixtures, diastereomers, or enantiomers thereof.

2. The compound of claim 1 wherein $R_1$ is one to four substituents independently selected from the group consisting of hydrogen, $C_{1-4}$alkyl (optionally substituted on a terminal carbon atom with a substituent selected from the group consisting of hydroxy and (halo)$_{1-3}$), $C_{1-4}$alkoxy (optionally substituted on a terminal carbon atom with (halo)$_{1-3}$), halogen, and hydroxy.

3. The compound of claim 1, wherein $R_1$ is one to two substituents independently selected from the group consisting of hydrogen, methyl, methoxy, chlorine, fluorine, and hydroxy.

4. The compound of claim 1, wherein $R_1$ is selected from the group consisting of hydrogen, chlorine, and fluorine.

5. The compound of claim 1, wherein $R_2$ is selected from the group consisting of —$NR_4$COAr, —$NR_4$CO-heteroaryl, —$NR_4$Ar, —CH=CH—Ar, —CF=CH—Ar, —CH=CF—Ar, —CCl=CH—Ar, —CH=CCl—Ar, —CH=CH-heteroaryl, —CF=CH-heteroaryl, —CH=CF-heteroaryl, —CCl=CH-heteroaryl, —CH=CCl-heteroaryl, and —$NR_4CH_2$Ar.

6. The compound of claim 1, wherein $R_2$ is —$NR_4$COAr.

7. The compound of claim 1, wherein $R_2$ is —NHCOAr.

8. The compound of claim 1, wherein Ar is selected from the group consisting of phenyl and naphthyl optionally substituted with one to four substituents independently selected from the group consisting of $C_{1-8}$alkyl (optionally substituted on a terminal carbon atom with a substituent selected from the group consisting of aryl, heteroaryl, amino (optionally substituted with one to two substituents selected from $C_{1-8}$alkyl), hydroxy and (halo)$_{1-3}$), $C_{1-8}$alkoxy (optionally substituted on a terminal carbon atom with a substituent selected from the group consisting of aryl, hydroxy and (halo)$_{1-3}$), aryl, heteroaryl, amino (optionally substituted with one to two substituents selected from $C_{1-8}$ alkyl), halogen, and hydroxy;

wherein aryl, heteroaryl and the aryl and heteroaryl portions of any of the foregoing substituents are optionally substituted with one to four substituents independently selected from the group consisting of $C_{1-8}$alkyl (optionally substituted on a terminal carbon atom with a substituent selected from the group consisting of amino (optionally substituted with one to two substituents selected from $C_{1-8}$alkyl), hydroxy and (halo)$_{1-3}$), $C_{1-8}$alkoxy (optionally substituted on a terminal carbon atom with a substituent selected from the group consisting of hydroxy and (halo)$_{1-3}$), amino (optionally substituted with one to two substituents selected from $C_{1-8}$ alkyl), $C_{1-8}$ alkylsulfonyl, $C_{1-8}$ alkylsulfinyl, $C_{1-8}$ alkylthio, cyano, halogen, and hydroxy.

9. The compound of claim 1, wherein Ar is phenyl optionally substituted with one to four substituents independently selected from the group consisting of $C_{1-4}$alkyl (optionally substituted on a terminal carbon atom with a substituent selected from the group consisting of amino (optionally substituted with one to two substituents selected from $C_{1-4}$alkyl), hydroxy and (halo)$_{1-3}$), $C_{1-4}$alkoxy (optionally substituted on a terminal carbon atom with a substituent selected from the group consisting of hydroxy and (halo)$_{1-3}$), aryl, heteroaryl, amino (optionally substituted with one to two substituents selected from $C_{1-4}$alkyl), halogen and hydroxy;

wherein the aryl and heteroaryl substituents are optionally substituted with one to four substituents independently selected from the group consisting of $C_{1-4}$alkyl (optionally substituted on a terminal carbon atom with a substituent selected from the group consisting of hydroxy and (halo)$_{1-3}$), $C_{1-4}$alkoxy (optionally substituted on a terminal carbon atom with a substituent selected from the group consisting of hydroxy and (halo)$_{1-3}$), amino (optionally substituted with one to two substituents selected from $C_{1-4}$ alkyl), halogen, and hydroxy.

10. The compound of claim 1, wherein Ar is phenyl optionally substituted with one to two substituents independently selected from the group consisting of $C_{1-4}$alkyl, phenyl, halogen and trifluoro($C_{1-4}$)alkyl; wherein phenyl is optionally substituted by $C_{1-4}$alkyl or halogen.

11. The compound of claim 1, wherein $R_3$ is one to two substituents independently selected from the group consisting of hydrogen, $C_{1-4}$alkyl (optionally substituted on a terminal carbon atom with a substituent selected from the group consisting of amino (optionally substituted with one to two substituents selected from $C_{1-4}$alkyl), hydroxy and (halo)$_{1-3}$), $C_4$alkoxy (optionally substituted on a terminal carbon atom with a substituent selected from the group consisting of hydroxy and (halo)$_{1-3}$), amino (optionally substituted with one to two substituents selected from $C_{1-4}$ alkyl), halogen, and hydroxy.

12. The compound of claim 1, wherein $R_3$ is one to two substituents independently selected from the group consisting of hydrogen, $C_{1-4}$ alkyl, trifluoro($C_{1-4}$)alkyl, $C_{1-4}$alkoxy, trifluoro($C_{1-4}$)alkoxy, halogen, and hydroxy.

13. The compound of claim 1, wherein $R_3$ is one to two substituents independently selected from the group consisting of hydrogen, methoxy, chlorine, fluorine, and hydroxy.

14. The compound of claim 1, wherein $R_4$ is hydrogen or $C_{1-4}$ alkyl.

15. The compound of claim 1, wherein $R_4$ is hydrogen.

16. The compound of claim 1, wherein Y is CH.

17. The compound of claim 1 wherein Z is —C(O)—.

18. A compound of claim 1, wherein the heteroaryl is a 5 membered ring, containing one nitrogen, oxygen, or sulfur and, optionally, up to two additional nitrogens.

19. A compound of claim 1, wherein the heteroaryl is a 6 membered ring, containing from one to three nitrogen atoms, wherein no more than two of three N are adjacent.

20. A compound of claim 1, wherein the heteroaryl is furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, or pyrazinyl.

21. A compound of claim 1, wherein the fuse heteroaryl is indolyl, isoindolyl, indolinyl, benzofuryl, benzothienyl, indazolyl, benzimidazolyl, benzthiazolyl, benzoxazolyl, benzisoxazolyl, benzothiadiazolyl, benzotriazolyl, quinolizinyl, quinolinyl, isoquinolinyl, or quinazolinyl.

22. A compound of Formula (II), Formula (III), or Formula (IV):

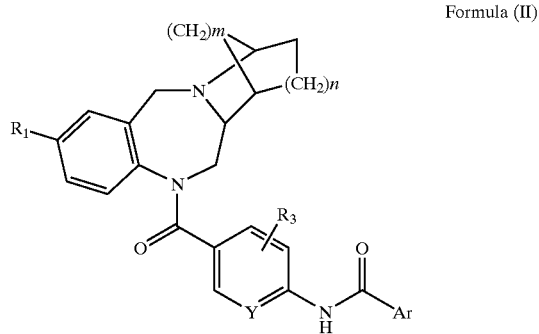

Formula (II)

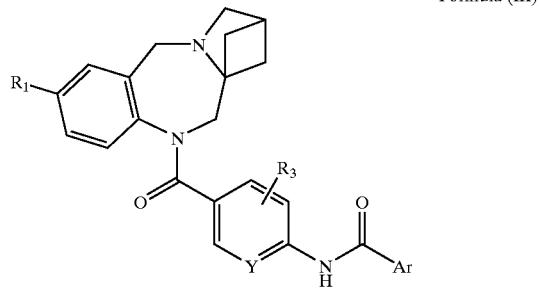

Formula (III)

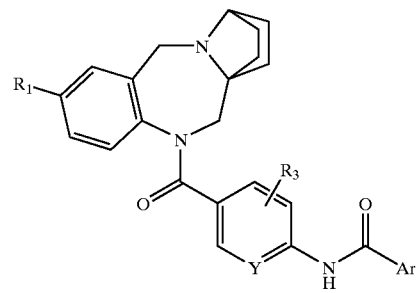

Formula (IV)

wherein
$R_1$ is one to four substituents independently selected from the group consisting of hydrogen, $C_{1-8}$alkyl (optionally substituted on a terminal carbon atom with a substituent selected from the group consisting of aryl, heteroaryl, hydroxy and (halo)$_{1-3}$), $C_{1-8}$alkoxy (optionally substituted on a terminal carbon atom with a substituent selected from the group consisting of hydroxy and (halo)$_{1-3}$), $C_{2-8}$alkenyl, $C_{2-8}$alkynyl, aryl, heteroaryl, halogen, and hydroxy;

Ar is selected from the group consisting of aryl and heteroaryl optionally substituted with one to five substituents independently selected from the group consisting of $C_{1-8}$alkyl (optionally substituted on a terminal carbon atom with a substituent selected from the group consisting of aryl, heteroaryl, amino (optionally substituted with one to two substituents selected from $C_{1-8}$alkyl), hydroxy and (halo)$_{1-3}$), $C_{1-8}$alkoxy (optionally substituted on a terminal carbon atom with a substituent selected from the group consisting of aryl, hydroxy and (halo)$_{1-3}$), aryl, heteroaryl, carboxyl, amino (optionally substituted with one to two substituents selected from $C_{1-8}$ alkyl), $C_{1-8}$ alkylsulfonyl, $C_{1-8}$ alkylsulfinyl, thio (substituted with a substituent selected from the group consisting of $C_{1-8}$alkyl and (halo)$_{1-3}$($C_{1-8}$)alkyl), cyano, halogen, hydroxy, and nitro;

wherein aryl, heteroaryl and the aryl and heteroaryl portions of any of the foregoing substituents are optionally substituted with one to four substituents independently selected from the group consisting of $C_{1-8}$alkyl (optionally substituted on a terminal carbon atom with a substituent selected from the group consisting of amino (optionally substituted with one to two substituents selected from $C_{1-8}$alkyl), hydroxy and (halo)$_{1-3}$), $C_{1-8}$alkoxy (optionally substituted on a terminal carbon atom with a substituent selected from the group consisting of hydroxy and (halo)$_{1-3}$), carboxyl, amino (optionally substituted with one to two substituents selected from $C_{1-8}$ alkyl), $C_{1-8}$ alkylsulfonyl, $C_{1-8}$ alkylsulfinyl, $C_{1-8}$ alkylthio, cyano, halogen, hydroxy, and nitro;

$R_3$ is one to three substituents independently selected from the group consisting of hydrogen, $C_{1-8}$alkyl (optionally substituted on a terminal carbon atom with a substituent selected from the group consisting of amino (optionally substituted with one to two substituents selected from $C_{1-8}$alkyl), hydroxy and (halo)$_{1-3}$), $C_{1-8}$alkoxy (optionally substituted on a terminal carbon atom with a substituent selected from the group consisting of hydroxy and (halo)$_{1-3}$), amino (optionally substituted with one to two substituents selected from $C_{1-8}$ alkyl), halogen, and hydroxy; and, Y is CH or N;

m is an integer selected from 1 or 2;

n is an integer selected from 0, 1 or 2; and heteroaryl is an aromatic ring of 5 or 6 members wherein the ring consists of carbon atoms and 1–3 heteroatoms selected from the group consisting of nitrogen, oxygen, and sulfur, said heteroaryl optionally fused to: 1) a benzene ring; 2) a 5 or 6 membered heteroaryl ring containing one of O, S or N and, optionally, one additional N; 3) a 5 to 7 membered alicyclic ring; or 4) a 5 to 7 membered heterocyclo ring, said ring being not further fused;

or pharmaceutically acceptable salts, racemic mixtures, diastereomers, or enantiomers thereof.

23. The compound of claim 22 wherein $R_1$ is one to four substituents independently selected from the group consisting of hydrogen, $C_{1-4}$alkyl (optionally substituted on a terminal carbon atom with a substituent selected from the group consisting of hydroxy and (halo)$_{1-3}$), $C_{1-4}$alkoxy (optionally substituted on a terminal carbon atom with (halo)$_{1-3}$), halogen, and hydroxy.

24. The compound of claim 22 wherein $R_1$ is one to two substituents independently selected from the group consisting of hydrogen, methyl, methoxy, chlorine, fluorine, and hydroxy.

25. The compound of claim 22 wherein $R_1$ is hydrogen, chlorine, or fluorine.

26. The compound of claim 22 wherein Ar is selected from the group consisting of phenyl and naphthyl optionally substituted with one to four substituents independently selected from the group consisting of $C_{1-8}$alkyl (optionally substituted on a terminal carbon atom with a substituent selected from the group consisting of aryl, heteroaryl, amino (optionally substituted with one to two substituents selected from $C_{1-8}$alkyl), hydroxy and (halo)$_{1-3}$), $C_{1-8}$alkoxy (optionally substituted on a terminal carbon atom with a substituent selected from the group consisting of aryl, hydroxy and (halo)$_{1-3}$), aryl, heteroaryl, amino (optionally substituted with one to two substituents selected from $C_{1-8}$ alkyl), halogen, and hydroxy; wherein aryl, heteroaryl and the aryl and heteroaryl portions of any of the foregoing substituents are optionally substituted with one to four substituents independently selected from the group consisting of $C_{1-8}$alkyl (optionally substituted on a terminal carbon atom with a substituent selected from the group consisting of amino (optionally substituted with one to two substituents selected from $C_{1-8}$alkyl), hydroxy and (halo)$_{1-3}$), $C_{1-8}$alkoxy (optionally substituted on a terminal carbon atom with a substituent selected from the group consisting of hydroxy and (halo)$_{1-3}$), amino (optionally substituted with one to two substituents selected from $C_{1-8}$ alkyl), $C_{1-8}$ alkylsulfonyl, $C_{1-8}$ alkylsulfinyl, $C_{1-8}$ alkylthio, cyano, halogen, and hydroxy.

27. The compound of claim 22 wherein Ar is phenyl optionally substituted with one to four substituents independently selected from the group consisting of $C_{1-4}$alkyl (optionally substituted on a terminal carbon atom with a substituent selected from the group consisting of amino (optionally substituted with one to two substituents selected from $C_{1-4}$alkyl), hydroxy and (halo)$_{1-3}$), $C_{1-4}$alkoxy (optionally substituted on a terminal carbon atom with a substituent selected from the group consisting of hydroxy and (halo)$_{13}$), aryl, heteroaryl, amino (optionally substituted with one to two substituents selected from $C_{1-4}$ alkyl), halogen and hydroxy;

wherein the aryl and heteroaryl substituents are optionally substituted with one to four substituents independently selected from the group consisting of $C_{1-4}$alkyl (optionally substituted on a terminal carbon atom with a substituent selected from the group consisting of hydroxy and (halo)$_{1-3}$), $C_{1-4}$alkoxy (optionally substituted on a terminal carbon atom with a substituent selected from the group consisting of hydroxy and (halo)$_{1-3}$), amino (optionally substituted with one to two substituents selected from $C_{1-4}$ alkyl), halogen, and hydroxy.

28. The compound of claim 22 wherein Ar is phenyl optionally substituted with one to two substituents independently selected from the group consisting of $C_{1-4}$alkyl, phenyl, halogen and trifluoro($C_{1-4}$)alkyl; wherein phenyl is optionally substituted selected from the group consisting of $C_{1-4}$alkyl, and halogen.

29. The compound of claim 22 wherein $R_3$ is one to two substituents independently selected from the group consisting of hydrogen, $C_{1-4}$alkyl (optionally substituted on a terminal carbon atom with a substituent selected from the group consisting of amino (optionally substituted with one to two substituents selected from $C_{1-4}$alkyl), hydroxy and (halo)$_{1-3}$), $C_{1-4}$alkoxy (optionally substituted on a terminal carbon atom with a substituent selected from the group consisting of hydroxy and (halo)$_{1-3}$), amino (optionally substituted with one to two substituents selected from $C_{1-4}$ alkyl), halogen, and hydroxy.

30. The compound of claim 22 wherein $R_3$ is one to two substituents independently selected from the group consisting of hydrogen, $C_{1-4}$ alkyl, trifluoro($C_{1-4}$)alkyl, $C_{1-4}$alkoxy, trifluoro($C_{1-4}$)alkoxy, halogen, and hydroxy.

31. The compound of claim 22 wherein $R_3$ is one to two substituents independently selected from the group consisting of hydrogen, methoxy, chlorine, fluorine, and hydroxy.

32. The compound of claim 22 wherein Y is CH.

33. The compound of claim 22 wherein n is an integer selected from 1 or 2.

34. The compound of claim 22 wherein n is 1.

35. The compound of claim 22 selected from the group consisting of:

N-[4-[(6,6a,7,8,9,10-hexahydro-7,10-ethanopyrido[2,1-c][1,4]benzodiazepin-5(12H)-yl)carbonyl]phenyl]-[1,1'-biphenyl]-2-carboxamide;

N-[4-[(6,6a,7,8,9,10-hexahydro-7,10-ethanopyrido[2,1-c][1,4]benzodiazepin-5(12H)-yl)carbonyl]-3-chlorophenyl]-[1,1'-biphenyl]-2-carboxamide;

N-[4-[[(6aS)-6,6a,7,8,9,10-hexahydro-7,10-methanopyrido[2,1-c][1,4]benzodiazepin-5(12H)-yl]carbonyl]-3-chlorophenyl]-[1,1'-biphenyl]-2-carboxamide;

N-[4-[[(6aS)-6,6a,7,8,9,10-hexahydro-7,10-methanopyrido[2,1-c][1,4]benzodiazepin-5(12H)-yl]carbonyl]-3-chlorophenyl]-[1,1'-biphenyl]-2-carboxamide;

N-[4-[[(6aR)-6,6a,7,8,9,10-hexahydro-7,10-methanopyrido[2,1-c][1,4]benzodiazepin-5(12H)-yl]carbonyl]-3-chlorophenyl]-[1,1'-biphenyl]-2-carboxamide;

N-[4-[[(6aS)-2-chloro-6,6a,7,8,9,10-hexahydro-7,10-methanopyrido[2,1-c][1,4]benzodiazepin-5(12H)-yl]carbonyl]phenyl]-4'-methyl-[1,1'-biphenyl]-2-carboxamide;

N-[4-[[(6aS)-6,6a,7,8,9,10-hexahydro-7,10-methanopyrido[2,1-c][1,4]benzodiazepin-5(12H)-yl]carbonyl]-3-chlorophenyl]-4'-methyl-[1,1'-biphenyl]-2-carboxamide;

N-[4-[[(6aS)-2-chloro-6,6a,7,8,9,10-hexahydro-7,10-methanopyrido[2,1-c][1,4]benzodiazepin-5(12H)-yl]carbonyl]-3chlorophenyl]-4'-methyl-[1,1'-biphenyl]-2-carboxamide;

N-[4-[[(6aS)-2-chloro-6,6a,7,8,9,10-hexahydro-7,10-methanopyrido[2,1-c][1,4]benzodiazepin-5(12H)-yl]carbonyl]phenyl]-4'-fluoro-[1,1'-biphenyl]-2-carboxamide;

N-[4-[[(6aS)-2-chloro-6,6a,7,8,9,10-hexahydro-7,10-methanopyrido[2,1-c][1,4]benzodiazepin-5(12H)-yl]carbonyl]phenyl]-2-fluoro-benzamide;

N-[4-[[(6aS)-2-chloro-6,6a,7,8,9,10-hexahydro-7,10-methanopyrido[2,1-c][1,4]benzodiazepin-5(12H)-yl]carbonyl]phenyl]-2-chloro-benzamide;

N-[4-[[(6aS)-2-chloro-6,6a,7,8,9,10-hexahydro-7,10-methanopyrido[2,1-c][1,4]benzodiazepin-5(12H)-yl]carbonyl]-3-chlorophenyl]-2-(trifluoromethyl)-benzamide;

N-[4-[[(6aS)-6,6a,7,8,9,10-hexahydro-7,10-ethanopyrido[2,1-c[]1,4benzodiazepin-5(12H)-yl]carbonyl]-3-chlorophenyl]-[1,1'-biphenyl]-2-carboxamide;

N-4-[[(6aS)-6,6a,7,8,9,10-hexahydro-7,10-ethanopyrido[2,1-c][1,4]benzodiazepin-5(12H)-yl]carbonyl]chlorophenyl]-5-fluoro-2-methyl-benzamide;

N-[4-[[(6aS)-2-chloro-6,6a,7,8,9,10-hexahydro-7,10-ethanopyrido[2,1-c][1,4]benzodiazepin-5(12H)-yl]carbonyl]phenyl]2-chloro-benzamide; and N-4-[[(6aS)-2-Chloro-6,6a,7,8,9,10-hexahydro-7,10-ethanopyrido[2,1-c][1,4]benzodiazepin-5(12H)-yl]carbonyl]phenyl]-4'-methyl-[1,1'-biphenyl]-2-carboxamide.

36. A compound of claim 22, wherein the heteroaryl is a 5 membered ring, containing one nitrogen, oxygen, or sulfur and, optionally, up to two additional nitrogens.

37. A compound of claim 22, wherein the heteroaryl is a 6 membered ring, containing from one to three nitrogen atoms, wherein no more than two of three N are adjacent.

38. A compound of claim 22, wherein the heteroaryl is furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, or pyrazinyl.

39. A compound of claim 22, wherein the fuse heteroaryl is indolyl, isoindolyl, indolinyl, benzofuryl, benzothienyl, indazolyl, benzimidazolyl, benzthiazolyl, benzoxazolyl, benzisoxazolyl, benzothiadiazolyl, benzotriazolyl, quinolizinyl, quinolinyl, isoquinolinyl, or quinazolinyl.

40. A pharmaceutical composition comprising a pharmaceutically acceptable carrier and a compound of claim 1.

41. A process for making a pharmaceutical composition comprising mixing a compound of claim 1 and a pharmaceutically acceptable carrier.

42. A method for treating a subject in need of treatment for a condition that may be treated with a vasopressin antagonist comprising administering to the subject a therapeutically effective amount of a compound of claim 1, wherein said condition is hypertension, congestive heart failure, liver cirrhosis, or water retention.

43. A method for treating a vasopressin mediated disorder selected from the group consisting of hypertension, congestive heart failure, liver cirrhosis, and water retention comprising administering to a subject in need thereof a therapeutically effective amount of a compound of claim 1.

44. The method of claim 42 wherein the vasopressin mediated disorder is congestive heart failure.

45. The method of claim 42 wherein the therapeutically effective amount of the compound is from about 0.001 to about 300 mg/kg/day.

46. A method for treating a vasopressin mediated disorder in a subject in need thereof comprising administering to the subject a therapeutically effective amount of a pharmaceutical composition of claim 40, wherein said disorder is hypertension, congestive heart failure, liver cirrhosis, or water retention.

47. The method of claim 46 wherein the vasopressin mediated disorder is congestive heart failure.

48. The method of claim 46 wherein the therapeutically effective amount of the pharmaceutical composition is from about 0.001 to about 300 mg/kg/day.

* * * * *